(12) United States Patent
Johnson et al.

(10) Patent No.: US 7,348,401 B2
(45) Date of Patent: Mar. 25, 2008

(54) PEPTIDES THAT INHIBIT COMPLEMENT ACTIVATION

(75) Inventors: Richard J. Johnson, Mundelein, IL (US); Shelley A. Maves, Mokena, IL (US)

(73) Assignee: Innate Biotech, Inc., Solana Beach, CA (US)

( * ) Notice: Subject to any disclaimer, the term of this patent is extended or adjusted under 35 U.S.C. 154(b) by 164 days.

(21) Appl. No.: 10/937,912

(22) Filed: Sep. 10, 2004

(65) Prior Publication Data

US 2005/0090448 A1     Apr. 28, 2005

Related U.S. Application Data

(60) Provisional application No. 60/501,710, filed on Sep. 10, 2003.

(51) Int. Cl.
    *A61K 36/00*      (2006.01)

(52) U.S. Cl. ...................................... 530/326

(58) Field of Classification Search ................... 514/15
See application file for complete search history.

(56) References Cited

U.S. PATENT DOCUMENTS

| | | | |
|---|---|---|---|
| 4,916,219 A | 4/1990 | Linhardt et al. | |
| 5,661,015 A * | 8/1997 | Binger et al. ................ | 435/364 |
| 6,232,296 B1 | 5/2001 | Henry | |
| 6,319,897 B1 | 11/2001 | Lambris et al. | |
| 6,667,173 B2 * | 12/2003 | Kazlauskas et al. ..... | 435/320.1 |
| 6,703,364 B2 * | 3/2004 | Kalafatis et al. ............... | 514/12 |

FOREIGN PATENT DOCUMENTS

WO     WO 99/13899 A1     3/1999

OTHER PUBLICATIONS

Flynn, J.S., et al. "Vaccination with a Feline Immunodeficiency Virus Multiepitopic Peptide Induces Cell-Mediated and Humoral Immune Responses in Cats, but Does Not Confer Protection," Journal of Virology (1997), vol. 71, pp. 7586-7592.*

Johnson et al., "Development of Novel Inhibitors of Complement." *FASEB Journal*, vol. 18, No. 4-5, pp. abstract 777.6, 2004.

Kapil et al., "Synthetic Peptide As Inhibitors of Human Complement Activation." *Protein and Peptide Letters*, vol. 4, No. 6, pp. 405-408, 1997.

Adachi et al., "Effects of Cyclosporine, Aspirin, and Cobra Venom Factor on Discordant Cardiac Xenograft Survival in Rats." *Transplantation Proceedings*, vol. XIX, No. 1, pp. 1145-1148, 1987.

Ahrehstedt et al., "Enhanced Local Production of Complement Components in the Small Intestines of Patients with Crohn's Disease." *The New England Journal of Medicine*, vol. 322, No. 19, pp. 1345-1349, 1990.

Arumugam et al., "A Small Molecule C5a Receptor Antagonist Protects Kidneys from Ischemia/Reperfusion Injury in Rats." *Kidney International*, vol. 63, pp. 134-142, 2003.

Barohn et al., "Soluble Terminal Complement Components in Human Myasthenia Gravis." *Clinical Neurology and Neurosurgery*, vol. 95, pp. 285-290, 1993.

Beeley, N., "Peptidomimetics and Small-Molecule Drug Design: Towards Improved Bioavailability and In Vivo Stability." *Trends in Biotechnology*, vol. 12, pp. 213-216, 1994.

Biesecker et al., "Inhibition of Acute Passive Transfer Experimental Autoimmune Myasthenia Gravis with Fab Antibody to Complement $C6^1$." *The Journal of Immunology*, vol. 142, No. 8, pp. 2654-2659, 1989.

Blair et al., "Linkage of Cytotoxic Agents to Immunoglobulins." *Journal of Immunological Methods*, vol. 59, pp. 129-143, 1983.

Bonfanti et al., "$p21^{WAF1}$-derived Peptides Linked to an Internalization Peptide Inhibit Human Cancer Cell Growth[1]." *Cancer Research*, vol. 57, pp. 1442-1446, 1997.

Bradt et al., "Complement-dependent Proinflammatory Properties of the Alzheimer's Disease β-Peptide." *The Journal of Experimental Medicine*, vol. 188, No. 3, pp. 431-438, 1998.

Broughton et al., "Radioimmunoassay of Antibiotics and Chemotherapeutic Agents." *Clinical Chemistry*, vol. 22, No. 6, pp. 726-732, 1976.

Butler, V., "Drug Immunoassays." *Journal of Immunological Methods*, vol. 7, pp. 1-24, 1975.

Chenoweth, D., "Anaphylatoxin Formation in Extracorporeal Circuits." *Complement Inflammation*, vol. 3, pp. 152-165, 1986.

Cochrane, C., "The Role of Complement in Experimental Disease Models." *Springer Seminars in Immunopathology*, vol. 7, pp. 263-270, 1984.

Couser et al., "Complement and the Direct Mediation of Immune Glomerular Injury: A New Perspective." *Kidney International*, vol. 28, pp. 879-890, 1985.

Crestfield et al., "The Preparation and Enzymatic Hydrolysis of Reduced and S-Carboxymethylated Proteins." *The Journal of Biological Chemistry*, vol. 238, No. 2, pp. 622-627, 1963.

Cunningham et al., "High-Resolution Epitope Mapping of hGH-Receptor Interactions by Alanine-Scanning Mutagenesis." *Science Reports*, vol. 244, pp. 1081-1085, 1989.

Demling et al., "The Lung Inflammatory Response to Thermal Injury: Relationship Between Physiological and Histologic Changes." *Surgery*, vol. 52-59, vol. 106, No. 1, 1988.

Deppisch et al., "Fluid Phase Generation of Terminal Complement Complex as a Novel Index of Bioincompatibility." *Kidney International*, vol. 37, pp. 696-706, 1990.

Erlanger, B., "The Preparation of Antigenic Hapten-Carrier Conjugates: A Survey." *Methods in Enzymology*, vol. 70, pp. 85-104, 1980.

(Continued)

*Primary Examiner*—Cecilia J. Tsang
*Assistant Examiner*—Thomas S. Heard
(74) *Attorney, Agent, or Firm*—Senniger Powers

(57) ABSTRACT

The present invention relates to compositions, including pharmaceutical compositions that inhibit complement activation, and contain amino acid sequences $X_1$-$X_2$-$X_3$-W-E-$X_4$-$X_5$-$X_6$ and/or $Z_1$-$C_1$-$Z_2$-P-$Z_3$-$Z_4$-$C_2$-$Z_5$ as described. The invention further relates to methods of inhibiting complement activation in vivo or ex vivo by administering a pharmaceutical composition as described herein.

22 Claims, 14 Drawing Sheets

OTHER PUBLICATIONS

Fava et al., "Critical Role of Peripheral Blood Phagocytes and the Involvement of Complement in Tumour Necrosis Factor Enhancement of Passive Collagen-Arthritis." *Clin. Exp. Immunol*, vol. 94, pp. 261-266, 1993.

Feasby et al., "Complement Depletion Suppresses Lewis Rat Experimental Allergic Neuritis." *Brain Research*, vol. 419, pp. 97-103, 1987.

Gallinaro et al., "The Role of the Complement System in Trauma and Infection." *Surgery, Gynecology and Obstetrics*, vol. 174, pp. 435-440, 1992.

Gauthier et al., "Effect of Cationized Antibodies in Preformed Immune Complexes on Deposition and Persistence in Renal Glomeruli." *Journal of Experimental Medicine*, vol. 156, pp. 766-777, 1982.

Gelfand et al., "Alternative Complement Pathway Activation Increases Mortality in a Model of Burn Injury in Mice." *Journal of Clinical Investigation*, vol. 70, pp. 1170-1176, 1982.

Guttmann, D., "Genetics of Acute Rejection of Rat Cardiac Allografts and a Model of Hyperacute Rejection." *Transplantation*, vol. 17, No. 4, pp. 383-386, 1974.

Hack et al., "Elevated Plasma Levels of the Anaphylatoxins C3a and C4a are Associated with a Fatal Outcome in Sepsis." *The American Journal of Medicine*, vol. 86, pp. 20-26, 1989.

Hruby, V., "Conformational and Topographical Considerations in the Design of Biologically Active Peptides." *Biopolymers*, vol. 33, pp. 1073-1082, 1993.

Jones et al., "Expression of Complement Regulatory Molecules and Other Surface Markers on Neutrophils from Synovial Fluid and Blood of Patients with Rheumatoid Arthritis." *British Journal of Rheumatology*, vol. 33, pp. 707-712, 1994.

Kilgore et al., "The Complement System in Myocardial Ischaemia/Reperfusion Injury." *Cardiovascular Research*, vol. 28, pp. 437-444, 1994.

Knechtle et al., "The Effect of Cyclosporine, Total Lymphoid Irradiation, and Cobra Venom Factor on Hyperacute Rejection." *Heart Transplantation and Immunology*, vol. IV, No. 5, pp. 541-545, 1985.

Kojima et al., "Activation of Complement of Hemodialysis Membrane." *Nippon Jenzo Gakkai Shi*, vol. 31, pp. 91-97, 1989.

Kulkarni et al., "Covalent Binding of Methotrexate to Immunoglobulins and the Effect of Antibody—linked Drug on Tumor Growth in Vivo[1]." *Cancer Research*, vol. 41, pp. 2700-2706, 1981.

Kyte et al., "A Simple Method for Displaying the Hydropathic Character of a Protein." *Journal of Molecular Biology*, vol. 157, pp. 105-132, 1982.

Langlois et al., "Accentuated Complement Activation in Patient Plasma During the Adult Respiratory Distress Syndrome: A Potential Mechanism for Pulmonary Inflammation." *Heart and Lung*, vol. 18, pp. No. 1, pp. 71-84, 1989.

Lennon et al., "Role of Complement in the Pathogenesis of Experimental Autoimmune Myasthenia Gravis." *Journal of Experimental Medicine*, vol. 147, pp. 973-983, 1977.

Leventhal et al., "Prolongation of Cardiac Xenograft Survival by Depletion of Complement." *Transplantation*, vol. 55, No. 4, pp. 857-866, 1993.

Liszewski et al., "Control of the Complement System." *Advances in Immunology*, vol. 61, pp. 201-283, 1996.

Makrides, S., "Therapeutic Inhibition of the Complement System." *Pharmacological Reviews*, vol. 50, No. 1, pp. 59-87, 1989.

Matsushita, M., "The Lectin Pathway of the Complement System." *Microbiology Immunology*, vol. 40, pp. 887-893, 1996.

McClean, R., "Complement and Glomerulonephritis—An Update." *Pediatric Nephrology*, vol. 7, pp. 226-232, 1993.

Mollnes et al., "Complement Activation in Rheumatoid Arthritis Evaluated by C3dg and the Terminal Complement Complex." *Arthritis and Rheumatism*, vol. 29, No. 6, pp. 715-721, 1986.

Morrison et al., "Combinatorial Alanine-Scanning." *Current Opinion in Chemical Biology*, vol. 5, pp. 302-307, 2001.

Morrison D., "Transformation and Preservation of Competent Bacterial Cells by Freezing." *Methods in Enzymology*, vol. 68, pp. 326-331, 1979.

Nakano et al., "Myasthenia Gravis: Quantitative Immunocytochemical Analysis of Inflammatory Cells and Detection of Complement Membrane Attack Complex at the End-Plate in 30 Patients." *Neurology*, vol. 43, pp. 1167-1172, 1993.

Nangaku et al., "C6 Mediates Chronic Progression of Tubulointerstitial Damage in Rates with Remnant Kidneys." *Journal of American Society of Nephrology*, vol. 13, pp. 928-936, 2002.

Niculescu et al., "The Role of Complement Activation in Atherosclerosis." *Immunologic Research*, vol. 30, No. 1, pp. 73-80, 2004.

Nomoto et al., "Improvement of Intestinal Absorption of Peptide Drugs by Glycosylation: Transport of Tetrapeptide by the Sodium Ion-Dependent $_D$-glucose Transporter." *Journal of Pharmaceutical Sciences*, vol. 87, No. 3, pp. 326-332, 1998.

Pauletti et al., "Improvement of Oral Peptide Bioavailability: Peptidomimetics and Prodrug Strategies." *Advanced Drug Delivery Reviews*, vol. 27, pp. 235-256, 1997.

Pekna et al., "Evidence for iC3 Generation During Cardiopulmonary Bypass as the Result of Blood-Gas Interaction." *Clinical Experimental Immunology*, vol. 91, pp. 404-409, 1993.

Playfair et al., "Production of Antibodies and Binding Reagents." *British Medical Bulletin*, vol. 30, pp. 24-31, 1974.

Robbins et al., "Activation of the Complement System in the Adult Respiratory Distress Syndrome." *American Review Respiratory Disorder*, vol. 135, pp. 651-658, 1987.

Salama et al., "Deposition of Terminal C5b-9 Complement Complexes on Erythrocytes and Leukocytes During Cardiopulmonary Bypass." *The New England Journal of Medicine*, vol. 318, pp. 408-414, 1988.

Sato et al., "The Terminal Sequence of Complement Plays an Essential Role in Antibody-Mediated Renal Cell Apoptosis." *Journal of the American Society of Nephrology*, vol. 10, pp. 1242-1252, 1999.

Schreiber et al., "Role of Antibody and Complement in the Immune Clearance and Destruction of Erythrocytes." *The Journal of Clinical Investigation*, vol. 51, pp. 575-582, 1972.

Sengeløv, H., "Complement Receptors in Neutrophils." *Critical Reviews in Immunology*, vol. 15, No. 2, pp. 107-131, 1995.

Song et al., "Complement Receptor 2-Mediated Targeting of Complement Inhibitors to Sites of Complement Activation." *The Journal of Clinical Investigation*, vol. 111, No. 12, pp. 1875-1885, 2003.

Spiegel et al., "Strategies for Inhibition of Complement Activation in the Treatment of Neurodegenerative Diseases." *Neuroinflammation: Mechanisms and Management*, pp. 129-176, 1998.

Strachan et al., "Inhibition of Immun-Complex Mediated Dermal Inflammation in Rats Following Either Oral or Topical Administration of a Small Molecule C5a Receptor Antagonist." *British Journal of Pharmacology*, vol. 134, pp. 1778-1786, 2001.

Thai et al., "Expression and Characterization of the C345C/NTR Domains of Complement Components C3 and C5[1]." *The Journal of Immunology*, vol. 171, pp. 6565-6573, 2003.

Thijs et al., "Activation of the Complement System During Immunotherapy with Recombinant IL-2." *The Journal of Immunology*, vol. 144, No. 6, pp. 2419-2424, 1990.

Vasthare et al., "Involvement of the Complement System in Cerebral Ischemic and Reperfusion Injury." *Federation of American Experimental Biology Journal*, vol. 7, A424.

Vriesendorp et al., "Complement Depletion Affects Demyelination and Inflammation in Experimental Allergic Neuritis." *Journal of Neuroimmunology*, vol. 58, pp. 157-165, 1995.

Wang et al., "Immunofluorescent Localization of Pig Complement Component 3, Regardless of the Presence or Absense of Detectable Immunoglobulins, in Hyperacutely Rejected Heart Xenografts." *Histochemical Journal*, vol. 24, pp. 102-109, 1992.

Wang et al., "Prodrug Approaches to the Improved Delivery of Peptide Drugs." *Current Pharmaceutical Design*, vol. 5, pp. 265-287, 1999.

Wang et al., "Amelioration of Lupus-Like Autoimmune Disease in NZB/W F₁ Mice After Treatment with a Blocking Monoclonal Antibody Specific For Complement Component C5." *Procedure National Academic Science USA*, vol. 93, pp. 8563-8568, 1996.

Wang et al., "Structural and Biological Characterization of Pegylated Recombinant Interferon Alpha-2b and its Therapeutic Implications." *Advanced Drug Delivery Reviews*, vol. 54, pp. 547-570, 2002.

Watson et al., "Genetic Susceptibility to Murine Collagen II Autoimmune Arthritis." *Journal of Experimental Medicine*, vol. 162, pp. 1878-1891, 1985.

Weinryb et al., "Metabolic and Analytic Considerations in the Design of Immunoassays." *Drug Metabolism Reviews*, vol. 10, No. 2, pp. 271-283, 1979.

Williams et al., "Immunology of Multiple Sclerosis." *Clinical Neuroscience*, vol. 2, pp. 2, 229-245, 1994.

Yasojima et al., "Up-Regulated Production and Activation of the Complement System in Alzheimer's Disease Brain." *American Journal of Pathology*, vol. 154, No. 3, pp. 927-936, 1999.

Zhang et al., "Targeting of Functional Antibody-Decay-Accelerating Factor Fusion Proteins to a Cell Surface." *The Journal of Biological Chemistry*, vol. 276, No. 29, pp. 27290-27295, 2001.

Zhao et al., "A Paradigm for Drug Discovery Using a Conformation From the Crystal Structure of a Presentation Scaffold." *Nature Structural Biology*, vol. 2, No. 12, pp. 1131-1137, 1995.

Zhou et al., "Predominant Role for C5b-9 in Renal Ischemia/Reperfusion Injury." *The Journal of Clinical Investigation*, vol. 105, No. 10, pp. 1363-1371, 2000.

Zilow et al., "Complement Activation and the Prognostic Value of C3a in Patients at Risk of Adult Respiratory Distress Syndrom." *Clinical and Experimental Immunology*, vol. 79, pp. 151-157, 1990.

\* cited by examiner

PEPTIDES THAT INHIBIT COMPLEMENT ACTIVATION

FIELD OF THE INVENTION

The present invention generally relates to polypeptides that specifically bind complement component C5 and inhibit complement activation. The invention further relates to a method of inhibiting complement activation in vivo or ex vivo by administering a pharmaceutical composition that inhibits complement activation.

BACKGROUND

The human immune system is equipped with several defense mechanisms to respond to bacterial, viral, or parasitic infection and injury. One of such defense mechanisms is the complement system, which plays a role both in innate and acquired immunity (see e.g. Cooper (1985), Adv. Immunol. 61:201-283; Liszewski et al. (1996), Adv. In Immunol. 61:201-282; Matsushita (1996), Microbiol. Immunol. 40:887-893; Sengelov (1995), Critical Review in Immunol. 15:107-131). The complement system directly and indirectly contributes to both innate inflammatory reactions as well as cellular (i.e. adaptive) immune responses. This array of effector functions is due to the activity of a number of complement components and their receptors on various cells. One of the principal functions of complement is to serve as a primitive self-nonself discriminatory defense system. This is accomplished by coating a foreign material with complement fragments and recruiting phagocytic cells that attempt to destroy and digest the "intruder".

Complement refers to a group of plasma proteins that are known to be necessary for antibody-mediated bactericidal activity. The complement system is composed of more than 30 distinct plasma and membrane bound proteins involving three separate pathways: classical, alternative and the lectin pathway. The C3 protein sits at the juncture of the classical and alternative pathways and represents one of the critical control points. Cleavage of C3 yields C3a and C3b. C3b molecules then react with a site on the C4b protein, creating a C3b-C4b•C2b complex that acts as a C5 convertase. Proteolytic activation of C5 occurs only after it is bound to the C3b portion of the C5 convertase on the surface of an activator (e.g., the immune complex). Like C3, C5 is also cleaved by C2b to produce fragments designated C5a (16,000 Da) and C5b (170,000 Da). The C5b molecule combines with the proteins of the terminal components to form the membrane attack complex described below. C5a is a potent inflammatory mediator and is responsible for many of the adverse reactions normally attributed to complement activation in various clinical settings.

The classical pathway (CP) of complement activation is activated primarily by immune complexes (ICs), but also by other proteins such as C-Reactive Protein, Serum Amyloid Protein, amyloid fibrils, and apoptotic bodies (Cooper, 1985).

The lectin pathway, discovered in the 1990s (Matsushita, 1996) is composed of lectins like mannose binding protein (or mannan binding lectin, MBL) and two MBL-associated serine proteases (MASP-1 and MASP-2) (see Wong et al, 1999). Upon activation of MBL•MASP-1•MASP-2, the MASP protease components cleave C4 and C2 forming a CP C3 convertase described above.

In the alternative pathway (AP) of complement activation, C3 is cleaved to form C3b in a mostly hydrolyzed and inactivated form. This process has been termed "C3 tick-over," a continuous and spontaneous process that ensures that whenever an activating surface (a bacterium, biomaterial, etc) presents itself, reactive C3b molecules will be available to mark the surface as foreign. Eventually, a C3b molecule attaches to one of the C3 convertase sites by direct attachment to the C3b protein component of the enzyme. This C3b-C3b•Bb complex is the alternative pathway C5 convertase and, in a manner reminiscent of the CP C5 convertase, converts C5 to C5b and C5a.

All three pathways lead to a common point: cleavage of C5 to produce C5b and C5a. C5a is a potent inflammatory mediator. The production of C5b initiates the formation of a macromolecular complex of proteins called the membrane attack complex (MAC) that disrupts the cellular lipid bilayer, leading to cell death. Even at sublytic levels, formation of MAC on host cells results in a number of activation responses (elevated $Ca^{+2}$, arachadonic acid metabolism, cytokine production).

Various types of control mechanisms have evolved to regulate the activity of the complement system at numerous points in the cascade (Liszewski et al, 1996). These mechanisms and include: 1) decay (dissociation) of converatase complexes, 2) proteolytic degradation of active components that is facilitated by several cofactors, 3) protease inhibitors, and 4) association of control proteins with terminal components that interfere with MAC formation. Without these important control elements, unregulated activation of the cascade results in overt inflammatory damage to various tissues and has been demonstrated to contribute to the pathology of many diseases.

Except for the cytotoxic action of the MAC, most of the biological responses elicited by complement proteins result from ligand-receptor-mediated cellular activation (Sengelov, 1995). The ability of complement to function in the opsonization of foreign elements is accomplished in large part by a set of receptors that recognize various C3 and C4 fragments bound to these foreign surfaces. These proteins help mediate the cell-cell interactions necessary for such activities as chemotaxis and cytotoxic killing.

In contrast to the above-discussed ligands, which remain attached to activating surfaces, C3a, C4a, and C5a are small cationic polypeptides that diffuse into the surrounding medium to activate specific cells. These peptides are called anaphylatoxins because they stimulate histamine release from mast cells and cause smooth muscle contraction, which can produce increased vascular permeability and lead to anaphylactic shock. These activities are lost when the peptides are converted to their des arg analogs (i.e., with the loss of their carboxyl terminal arginine residue). This occurs rapidly in vivo and is catalyzed by serum carboxypeptidase N.

In addition to its anaphylatoxic properties, C5a and C5a-desarg bind to specific receptors originally found on neutrophils and monocytes. Recently the receptors for both C5a and C3a have been cloned and sequenced. The C5aR (CD88) has been shown to be expressed on endothelial cells (EC), hepatocytes, epithelial cells (lung and kidney tubules), T cells, cells in the CNS as well as on the myeloid cell lines. In addition, expression levels of C5aRs are increased on EC and hepatocytes by exposure to LPS and IL-6. In myeloid cells (neutrophils and monocytes), the C5a-receptor interaction leads to a variety of responses, including chemotaxis of these cells into an inflammatory locus; activation of the cells to release the contents of several types of secretory vesicles and produce reactive oxygen species that mediate cell killing; increased expression of CR1, CR3, and LFA-1, resulting in cellular hyperadherence; and the production of other mediators such as various arachidonic acid metabolites and cytokines, e.g., IL-1, -6, and -8. Many of the adverse reactions seen during extracorporeal therapies, such as hemodialysis, are directly attributable to C5a production. C3aRs are expressed on a variety of cell types including eosinophils, neutrophils, monocytes, mast cells, astrocytes (in the CNS), as well as γ-IFN-activated T cells. In eosinophils, C3a elicits responses similar to C5a, including intracellular calcium elevation, increases endothelial cell adhesion, and the generation of reactive oxygen intermediates.

While complement is beneficial for fighting against pathogens, inappropriate or excessive activation of the complement system can lead to inadvertent tissue damage and cytotoxic responses. In order to control this, nature has built into the complement system several control mechanisms utilizing both plasma and cell surface proteins to limit the amount of activation and prevent damage to host tissues. However, in several disease settings complement activation is not adequately controlled and results in tissue damage.

Over activation of the complement system has been shown to play a role in a wide range of diseases including autoimmune diseases such as: glomerulonephritis (McLean (1993) Pediatr. Nephrol. 7:226; Couser et al. (1985) Kidney Inst. 29:879; Nangaku et al. (2002) J. Am. Soc. Nephrol. 13:928-936; Sato et al. (1999) J. Am. Soc. Nephrol. 10:1242-1252); rheumatoid arthritis (Mollnes et al. (1986) Arthritis Rheum. 29:715; Jones et al. (1994) Br. J. Rheum. 33:707; Fava et al. (1993) Clin. Exp. Immunol. 94:261; Strachan et al. (2001) British J. Pharm. 134:1778-1786); type II collagen-induced arthritis (Watson & Townes (1985) J. Exp. Med. 162:1878); psoriasis (Strachan et al. 2001), systemic lupus erythamatosis (Wang et al. (1996) Proc. Natl. Acad. Sci. 93:8563; Stracha et al. 2001); transplantation rejection (Wang et al. (1992) Histochem. J. 24:102; Leventhal et al. (1993) Transplantation 55:857); hyperacute allograft and hyperacute xenograft rejection (Adachi et al. (1987) Trans. Proc. 19(1):1145; Knechtle et al. (1985) J. Heart Transplant 4(5):541; Guttman (1974) Transplantation 17:383); immune-complex-induced vasculitis (Cochrane (1984) Springer Seminar Immunopathol. 7:263); and myasthenia gravis (Nakano & Engel (1993) Neurology 43:1167; Barohn & Brey (1993) Clin. Neurol. Neurosurg. 95:285; Biesecker & Gomez (1989) J. Immunol. 142:2654; Lennon et al. (1978) J. Exp. Med. 147:973).

In addition, complement plays a role in ischemia reperfusion settings such as: myocardial infarction (Kilgore et al. (1994) Cardiovasc. Res. 28:437), stroke (Vasthare et al. (1993) FASEB J. 7:A424), atherosclerosis/vasculitis (Niculescu & Rus (2004) Immuno. Res. 30:73-80), renal ischemia/reperfusion (Zhou et al. (2000) J. Clinical Investigation 105:1363-1371; Arumugam et al. (2003) Kidney Intl. 63:134-142), and injury due to cardiopulmonary bypass surgery and post pump syndrome in cardiopulmonary bypass (Salama et al. (1988) N. Engl. J. Med. 318:408-14; Chenoweth et al. (1986) Complement 3:152-165; Chenoweth et al. (1981) Complement. Inflamm. 3:152-165).

Complement has also been shown to play a role in central nervous system diseases such as: multiple sclerosis (Williams et al. (1994) Clin. Neurosci. 2:229), Alzheimer's disease (Bradt et al. (1998) J. Exp. Med. 188:431; Yasoshima et al. (1999) Am. J. Pathol. 154:927), and experimental allergic neuritis (Vriesendorp et al. (1995) J. Neuroimmunol. 58:157; Feasby et al. (1987) Brain Res. 419:97).

Various other diseases, disorders, or injury that complement has been linked to include but are not limited to: fatal complication in sepsis (Hack et al. (1989) Am. J. Med. 86:20-26); hemolytic anemia (Schreiber & Frank (1972) J. Clin. Invest. 51:575); adult respiratory distress syndrome (Zilow et al. (1990) Clin. Exp. Immunol. 79:151-57; Langlois et al. (1989) Heart Lung 18:71-84; Robbins et al. (1987) Am. Rev. Respir. Dis. 135:651); thermal injury (burn, frostbite) (Gallinaro et al. (1992) Surg. Gynecol. Obstet. 174:435; Gelfand et al. (1982) J. Clin. Invest. 70:1170; Demling et al. (1989) Surgery 106:52-9); extracorporeal dialysis and blood oxygenation (Pekna et al. (1993) Clin. Exp. Immunol. 91:404; Deppisch et al. (1990) Kidney Inst. 37:696-706; Kojima et al. (1989) Nippon Jenzo Gakkai Shi 31:91-97); intestinal inflammation of Crohn's disease which is characterized by the lymphoid infiltration of mononuclear and polymorphonuclear leukocytes (Ahrenstedt et al. (1990) New Engl. J. Med. 322:1345-1349); and toxicity and side effects observed from recombinant IL-2 immunotherapy treatment (Thijs et al. (1990) J. Immunol. 144:2419), and complement activation known to occur in monoclonal antibody therapy.

In many of the diseases, disorders, and injuries listed above, experiments have shown that inhibition of complement activation can stop the progression of the disease, disorder, or injury and, in some cases, even reverse some of the damage already sustained. Thus, compounds that potently and selectively inhibit the complement cascade and/or its various components and factors will have therapeutic applications in several diseases, disorders, or injuries, including those listed above (Makrides (1998) Pharmacol. Rev. 50:59-87; Spiegel et al., Strategies for Inhibition of Complement Activation in the Treatment of Neurodegenerative Diseases in: Neuroinflammation: Mechanisms and Management, Wood (ed.), Humana Press, Inc., Totowa, N.J., Chapter 5, pp. 129-176; and U.S. Pat. No. 4,916,219; U.S. Pat. No. 6,319,897; U.S. Pat. No. 6,515,002; U.S. Pat. No. 6,232,296).

SUMMARY OF THE INVENTION

Among the various aspects of the present invention is the provision of potent inhibitors of complement, which possess greater bioavailability and fewer side effects than currently available inhibitors. Briefly, therefore, the present invention is directed to newly identified potent complement system inhibitors that are potentially valuable therapeutic agents for a variety of conditions.

In one embodiment, the present invention relates to a composition for the inhibition of complement activation, wherein the composition comprises a polypeptide, which in turn, comprises the sequence $X_1$-$X_2$-$X_3$-W-E-$X_4$-$X_5$-$X_6$, wherein E is a glutamic acid residue; W is a tryptophan residue; $X_1$ a hydrogen atom, one to five amino acid residues, or a bond covalently linking the polypeptide to another component of the composition; $X_2$ is an amino acid residue; $X_3$ is a residue of a basic amino acid; $X_4$ is a residue of an aromatic amino acid; $X_5$ is an amino acid residue; and $X_6$ a hydrogen atom, one to five amino acid residues, or a bond covalently linking the polypeptide to another component of the composition.

In another embodiment, the present invention relates to a composition for the inhibition of complement activation, wherein the composition comprises a polypeptide, which in turn, comprises the sequence $X_1$-$X_2$-$X_3$-W-E-$X_4$-$X_5$-$X_6$, wherein E is a glutamic acid residue; W is a tryptophan residue; $X_1$ is a hydrogen atom or an amino acid residue; $X_2$ is an amino acid residue; $X_3$ is a residue of a basic amino acid; $X_4$ is a residue of an aromatic amino acid; $X_5$ is an amino acid residue; and $X_6$ is a hydrogen atom, an amino acid residue, or a bond covalently linking the polypeptide to another component of the composition.

Another aspect of the invention is a method of inhibiting complement activation in a patient comprising administering to the patient the compositions of the invention.

In one embodiment, the present invention relates to a composition for the inhibition of complement activation, wherein the composition comprises a polypeptide, which in turn comprises the sequence $Z_1$-$C_1$-$Z_2$-P-$Z_3$-$Z_4$-$C_2$-$Z_5$, wherein $C_1$ and $C_2$ are cysteine residues; P is a proline residue; $Z_1$ is a hydrogen atom or an amino acid residue; $Z_2$ is at least one amino acid residue; $Z_3$ is a residue of a hydrophobic amino acid; $Z_4$ is at least one amino acid residue; and $Z_5$ is a hydrogen atom or an amino acid residue.

In another embodiment, the present invention relates to a composition for the inhibition of complement activation, wherein the composition comprises a polypeptide, which in turn comprises the sequence $Z_1$-$C_1$-$Z_2$-P-$Z_3$-$Z_4$-$C_2$-$Z_5$, wherein $C_1$ and $C_2$ are cysteine residues; P is a proline residue; $Z_1$ is a hydrogen atom, an amino acid residue, or a bond covalently linking the polypeptide to another component of the composition; $Z_2$ is at least one amino acid residue; $Z_3$ is a residue of a hydrophobic amino acid; $Z_4$ is at least one amino acid residue; and $Z_5$ is a hydrogen atom, an amino acid residue, or a bond covalently linking the polypeptide to another component of the composition.

Other objects and features will be in part apparent and in part pointed out hereinafter.

ABBREVIATIONS AND DEFINITIONS

Figure 1:
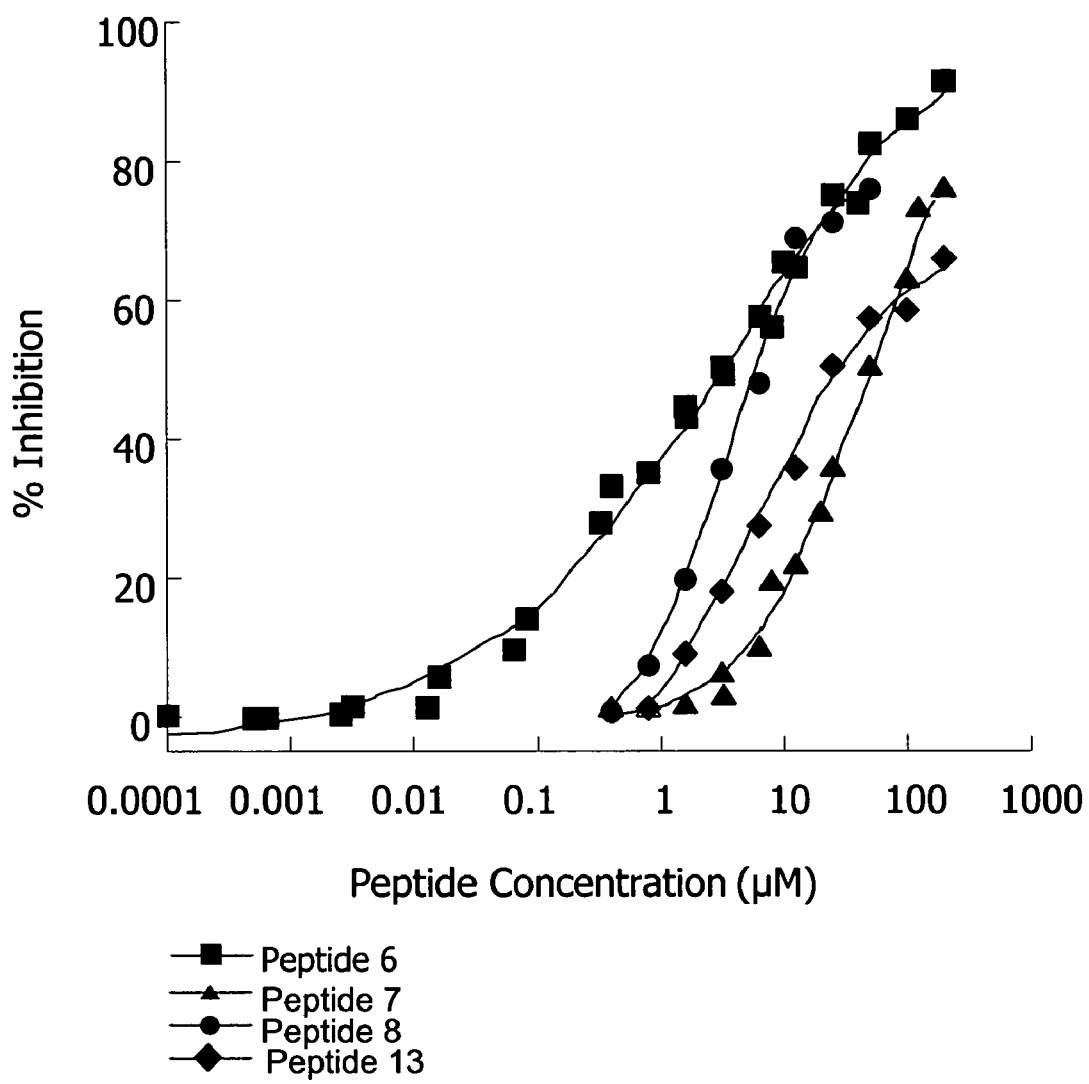
FIG. 1 is a line graph showing the dose dependent titration curve of percent inhibition of classical pathway hemolysis versus peptide concentration for peptides 6, 7, 8, and 13. See Example 3 for information regarding methodology.

The following definitions and methods are provided to better define the present invention and to guide those of ordinary skill in the art in the practice of the present invention. Unless otherwise noted, terms are to be understood according to conventional usage by those of ordinary skill in the relevant art.

The term "analog" as used herein refers to a molecule substantially similar in function to either the entire molecule or to a fragment thereof. An analog may contain chemical moieties that are not normally a part of the molecule, but that may, for example, improve the molecule's half-life or decrease its toxicity. Moieties capable of mediating such effects are disclosed in Remington's Pharmaceutical Sciences (1980).

The term "amino acid" is used herein in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids.

"BSA" is an abbreviation for bovine serum albumin.

As used herein, "complement-mediated lysis," "complement-dependent lysis," "complement-mediated cytotoxicity," or "complement-dependent cytotoxicity" all generally mean the process by which the complement cascade is activated, multi-component complexes are assembled, ultimately generating a lytic complex that has direct lytic action, causing cell permeabilization. Therapeutic agent-targeting agents for use in inducing complement-mediated lysis will generally include an antibody Fc portion.

The term "hydrophobic" when used in reference to amino acids refers to those amino acids which have nonpolar side chains. Hydrophobic amino acids include valine, leucine, isoleucine, cysteine and methionine. Three hydrophobic amino acids have aromatic side chains. Accordingly, the term "aromatic" when used in reference to amino acids refers to the three aromatic hydrophobic amino acids phenylalanine, tyrosine and tryptophan.

The term "inhibit" is used herein to mean reduce or prevent.

The term "inhibit complement" is used herein to mean that polypeptide of the composition binds to C5 and inhibits the proteolysis of C5 and/or the formation of MAC.

"PBS" is an abbreviation for phosphate buffered saline.

The term "pharmaceutically acceptable" is used adjectivally herein to mean that the modified noun is appropriate for use in a pharmaceutical product; that is the pharmaceutically acceptable material is relatively safe and/or non-toxic, though not necessarily providing a separable therapeutic benefit by itself.

As used herein, "polynucleotide" and "oligonucleotide" are used interchangeably and mean a polymer of at least 2 nucleotides joined together by phosphodiester bonds and may consist of either ribonucleotides or deoxyribonucleotides.

The term "polypeptide" when used herein refers to two or more amino acids that are linked by peptide bond(s), regardless of length, functionality, environment, or associated molecule(s). Typically, the polypeptide is at least four amino acid residues in length and can range up to a full-length protein. As used herein, "polypeptide," "peptide," and "protein" are used interchangeably.

"RBC" is an abbreviation for red blood cells.

As used herein, "sequence" means the linear order in which monomers occur in a polymer, for example, the order of amino acids in a polypeptide or the order of nucleotides in a polynucleotide.

The term "subject" for purposes of treatment includes any human or animal subject in need of complement inhibition. The subject can be a domestic livestock species, a laboratory animal species, a zoo animal, or a companion animal. In one embodiment, the subject is a mammal. In another embodiment, the mammal is a human being. The terms "subject" and "patient" are used interchangeably herein.

The phrase "therapeutically-effective" is intended to qualify the amount of an agent (e.g., a composition comprising a peptide as described herein) or combination of two or more agents (e.g., a mixture of peptides as described herein), which will achieve the goal of improvement in disorder severity and the frequency of incidence over no treatment.

The term "treatment" as used herein includes alleviation, elimination of causation of or prevention of undesirable symptoms associated with a complement activation-associated disease or disorder. Treatment as used herein includes prophylactic treatment.

The term "variant" as used herein refers to a molecule substantially similar in structure and biological activity or immunological properties to either the entire molecule or a fragment thereof. Thus, provided that two molecules possess a similar activity, they are considered variants even if the sequence of their amino acid residues is not identical.

For all the amino acid sequences disclosed herein, it is understood that equivalent nucleotides and amino acids can be substituted into the sequences without affecting the function of the sequences. Such substitutions is within the ability of a person of ordinary skill in the art.

DETAILED DESCRIPTION OF THE INVENTION

As the role complement plays in tissue damage and deterioration becomes better understood, more focus has been placed on developing inhibitors to controls these diseases. In accordance with the present invention, provided are compositions, useful for inhibiting complement activation in mammals, comprising identified polypeptides that specifically bind complement component C5 and effect complement activation and complement mediated effector functions that can lead to tissue damage. While generally the compositions of the invention inhibit complement in mammals (non-limiting examples include swine, primates, and humans), difficulties have been encountered in mice, rats, dogs, rabbit, and guinea pig, possibly stemming from limitations of complement component assays and/or differences of C5 sequences between different species.

In one aspect of the invention, identified polypeptides comprising the sequence $X_1$-$X_2$-$X_3$-W-E-$X_4$-$X_5$-$X_6$ (peptide "X") specifically bind C5 and inhibit formation of both C5b-9 and C5a. In another aspect of the invention, identified polypeptides comprising the sequence $Z_1$-$C_1$-$Z_2$-P-$Z_3$-$Z_4$-$C_2$-$Z_5$ (peptide "Z") specifically bind C5, inhibit formation of C5b-9, and elevate levels of C5a in certain pathway systems.

Several compositions of the present invention comprise a polypeptide that specifically binds to C5 and inhibits formation of both C5b-9 and C5a. In these compositions, the polypeptide in turn comprises a sequence of $X_1$-$X_2$-$X_3$-W-E-$X_4$-$X_5$-$X_6$.

In one composition of the invention, $X_1$ can be a hydrogen atom, one to five amino acid residues, or a bond covalently linking the polypeptide to another component of the composition.

In one embodiment, $X_1$ is a hydrogen atom. This hydrogen atom is attached to the terminal amino group of the amino acid residue at $X_2$. In this embodiment, the amino-terminus of the polypeptide sequence of the composition is the amino acid residue of $X_2$.

In another embodiment, $X_1$ is a peptide sequence consisting of from one to five amino acid residues. These amino acid residues can be selected from any of the naturally occurring amino acids such as proteogenic L-amino acids (i.e., the 20 amino acids normally incorporated into proteins) as well as D-amino acids and non-proteogenic amino acids. Non-proteogenic amino acids are generally metabolites or analogues of the proteogenic amino acids. Non-limiting examples of naturally occurring non-proteogenic amino acids include ornithine, taurine, hydroxyproline, hydroxylysine, norleucine, β-alanine, gamma amino butyric acid, selenocysteine, phosphoserine, pyroglutamic acid, and pyrrolysine. The X, amino acid may also be selected from non-naturally occurring amino acids. Non-naturally occurring amino acids include, but are not limited to, amino acid derivatives and analogs. Non-limiting examples of amino acid derivates include selenomethionine, telluro-methionine, and p-aminophenylalanine, fluorinated amino acids (e.g., fluorinated tryptophan, tyrosine and phenylalanine), nitrophenylalanine, nitrobenzoxadiazolyl-L-lysine, deoxymethylarginine, and cyclohexylalanine. Amino acid analogs include chemically synthesized compounds having properties known in the art to be characteristic of amino acids, examples of which include, but are not limited to, the tryptophan "analog" b-selenolo[3,2-b]pyrrolylalanine and the proline "analog" thiaproline (1,3-thiazolidine-4-carboxylic acid).

In one example, $X_1$ is three amino acid residues. For example, these three amino acid residues can be threonine, alanine, and glutamic acid; glutamic acid, alanine, and glutamic acid; leucine, alanine, and glutamic acid; threonine, glutamic acid, and glutamic acid; or threonine, leucine, and glutamic acid.

In another example, $X_1$ is one amino acid residue. For example, $X_1$ can be a glutamic acid, aspartic acid, isoleucine, leucine, or proline residue. In another example, $X_1$ is a glutamic acid residue. In exploring the amino acids in the $X_1$ position, a 10-mer peptide (Peptide 46, SEQ ID NO 46) was used as a basic structure and the residue at position $X_1$ was randomized (i.e. changed to every other amino acid) (see e.g. Example 11). Results showed strongest activity when $X_1$ was glutamic acid (Peptide 83, SEQ ID NO 83 and Peptide 84, SEQ ID NO 84). Substitutions for $X_1$ of comparable activity included aspartic acid (Peptide 13, SEQ ID NO 13), isoleucine (Peptide 90, SEQ ID NO 90), leucine (Peptide 91, SEQ ID NO 91), and proline (Peptide 95, SEQ ID NO 95). Substitution of asparagine at position $X_1$ (Peptide 54, SEQ ID NO 54) had little effect on the inhibitory activity.

In yet another embodiment of this composition, $X_1$ is a covalent bond linking the polypeptide to another component of the composition. These components will have a multiplicity of sites to which the peptides can be coupled. Such components may include, but are not limited to vitamins, proteins, polypeptides, carbohydrates, polysaccharides, lipids, lipopolysaccharides, nucleic acids, and biomaterials. Suitable vitamins include, but are not limited to, biotin. Vitamins, such as biotin, are known to promote delivery of agents into the blood. Furthermore, biotin/avidin systems are well known in the art (see e.g. Wilcheck and Bayer (1990), Methods of Enzymology 184 (Academic Press)). Suitable proteins include, but are not limited to, albumins (e.g., bovine serum albumin, ovalbumin, human serum albumin), immunoglobulins, thyroglobulins (e.g., bovine thyroglobulin), and hemocyanins (e.g., Keyhole Limpet hemocyanin). Suitable polypeptides include, but are not limited to, polylysine and polyalaninelysine. Suitable polysaccharides include, but are not limited to, dextrans of various sizes (e.g., 12,000 to 500,000 molecular weight). Suitable biomaterials include, but are not limited to, various artificial implants, pacemakers, valves, catheters, and membranes (e.g. dialyzer), as well as synthetic polymers such as polypropylene oxide (PPO) and polyethylene glycol (PEG).

Components coupled to the polypeptide of the composition may play a role in a variety of functions well known in the art. For example, components could include fusion constructs used for targeted delivery of complement inhibitors (see e.g. Song et al (2003), J. Clinical Investigation, 111(12): 1875-85; Zhang et al. (2001), J. Biol. Chem. 276(29):27290-95). Targeting could also occur through fusion of the composition with another peptide (see e.g. Cancer Research (1997) 57:1442-1446). In way of a further non-limiting example, when a biological molecule is protein-X1 . . . X6, a protein may be an antibody or a fragment thereof specific for a type of cells, thereby allowing for the targeting of X1 . . . X6 to that type of cells. Furthermore, coupling that is performed to increase the size of the biological molecule may be useful as larger molecules tend to have a longer plasma half-life. In a non-limiting example, components such as PEG (through pegylation of the polypeptide) could extend the in vivo half-life of complement inhibitor compositions (see e.g. Wang (2002), Advanced Drug Deliv. Reviews, 54:547-570). In yet another non-limiting example of coupling function, glycosylation (i.e. coupling the polypeptide to certain carbohydrates) can improve intestinal absorption of the polypeptide-containing composition of the invention (see e.g. J. Pharmaceutical Sciences (1998) 87(3):326-332).

The polypeptides of this composition may be covalently coupled to other components of the composition using methods and agents well known in the art. Suitable agents include glutaraldehyde, carbodiimide, cyanoborohydride, diimidoesters, periodate, alkylhalides, succinimides, dimethylpimelimidate and dimaleimides (see Blait and Ghose (1983) J. Immunol. Methods 59:129; Blair and Ghose (1981) Cancer Res. 41:2700; Gauthier et al. (1982) J. Exp. Med. 156:766-777). For a list of possible coupling agents, see generally Catalog And Handbook (1994-1995) and Products Catalog (1997), Pierce Chemical Co., Rockford, Ill. Additional references concerning carriers and techniques for coupling polypeptides thereto are: Erlanger (1980) Methods In Enzymology 70:85-104; Makela and Seppala (1986) Handbook of Experimental Immunology (Blackwell); Parker (1976) Radioimmunoassay of Biologically Active Compounds (Prentice-Hall); Butler (1974) J. Immunol. Meth. 7:1-24; Weinryb and Shroff (1979) Drug. Metab. Rev. 10:271-83; Broughton and Strong (1976) Clin. Chem. 22:726-32; Playfair et al. (1974) Br. Med. Bull. 30:24-31.

It is apparent that additional amino acid residues may be present between $X_1$ and any other component associated with the polypeptide sequence of the invention.

In several compositions of the invention, there exists an embodiment where $X_2$ is an amino acid residue, which can include natural and non-natural amino acids, analogs, and derivatives, as discussed previously. In another embodiment, $X_2$ is a hydrophobic amino acid. Hydrophobic amino acids are those amino acids which have nonpolar side chains, and include the natural amino acid residues of valine, leucine, isoleucine, cysteine and methionine, as well as those hydrophobic amino acids with aromatic side chains, which include phenylalanine, tyrosine and tryptophan. For example, the $X_2$ amino acid can be selected from among tryptophan, tyrosine, valine, threonine, isoleucine, alanine, glutamic acid, threonine, and leucine. As another example, the $X_2$ amino acid can be selected from among valine, threonine, leucine. In a preferred embodiment, the $X_2$ amino acid is valine. Analogs and derivatives of these amino acid residues, as discussed previously, are likewise included in this embodiment. In exploring various amino acids in the $X_2$ position, a 10-mer peptide was used as a basic structure (Peptide 46, SEQ ID NO 46) and the residue at position $X_2$ was randomized (i.e. changed to every other amino acid) (see e.g. Example 10, Example 15). These peptides were then tested in the RBC hemolysis assay. Results showed that all of these peptides displayed activity, but that a hydrophobic side chain at this position appeared to increase the activity compared to the parent peptide, while a charged amino acid side chain at this position appeared to diminish the inhibitory activity.

In several compositions of the invention, there exists an embodiment where $X_3$ is a residue of a basic amino acid. Basic amino acids have positively charged side chains and include arginine, histidine, and lysine. As an example, $X_3$ can be an arginine residue. Substitution experiments demonstrated that changing the arginine at position $X_3$ to either of two other basic amino acids, lysine or histidine (Peptide 55, SEQ ID NO 55 and Peptide 56, SEQ ID NO 56, respectively), slightly lowers the inhibiting activity of the parent peptide.

In keeping with traditional amino acid nomenclature, the W in the sequence above represents tryptophan. Conservative substitutions, for which methodology is well known in the art (see e.g. Example 9), for the tryptophan residue of the sequence resulted in complete loss of inhibitory activity.

In keeping with traditional amino acid nomenclature, the E in the sequence above represents glutamic acid. Conservative substitutions, for which methodology is well known in the art (see e.g. Example 9), for the glutamic acid residue of the sequence resulted in complete loss of inhibitory activity.

In one embodiment, $X_4$ is an aromatic amino acid residue. Aromatic amino acids include phenylalanine, tyrosine and tryptophan. As an example, $X_4$ can be phenylalanine. Conservative substitution experiments (see e.g. Example 9) demonstrated that substituting tyrosine for the phenylalanine at $X_4$ (Peptide 61, SEQ ID NO 61) resulted in minimal loss of activity, while further replacements produced more severe losses (tryptophan in Peptide 60, SEQ ID NO 60 or leucine in Peptide 64, SEQ ID NO 64).

In one embodiment, $X_5$ is an amino acid residue, which can include natural and non-natural amino acids, analogs, and derivatives, as discussed previously. In a preferred embodiment, $X_5$ is proline.

In various embodiments, $X_6$ can represent either a hydrogen atom, a sequence of one to five amino acid residues, or a bond covalently linking the polypeptide to another component of the composition. In one embodiment, $X_6$ is a hydrogen atom. This hydrogen atom is attached to the terminal carboxy group of the amino acid residue at $X_5$. In this embodiment, the carboxy-terminus of the polypeptide sequence of the composition is the amino acid residue of $X_5$. In another embodiment, $X_6$ is a sequence of one to five amino acid residues, which can include natural and non-natural amino acids, analogs, and derivatives, as discussed previously. For example, $X_6$ can be a sequence of three amino acid residues. As another example, $X_6$ can be one amino acid residue. In a further embodiment, $X_6$ is a covalent bond linking the polypeptide to another component of the composition. Such coupled components, their functions, and methods of linkage are as discussed previously.

It is apparent that additional amino acid residues may be present between $X_6$ and any other component associated with the polypeptide sequence of the invention.

In one embodiment, the polypeptide sequence has an amino-terminal acetyl group, and in another, the polypeptide sequence has a carboxy-terminal amide group, and in yet another, the polypeptide sequence has both an amino-terminal acetyl group and a carboxy-terminal amide group. Experiments have demonstrated that blocking the N-terminus (by acetylation) and the C-terminus (by amidation) of a polypeptide increased the inhibitory activity of this polypeptide, as measured by an RBC hemolysis assay (see e.g. Example 3, FIG. 7, FIG. 10). Methodology for making similar terminal modifications as discussed herein are well known in the art (Fields (1997), Methods in Enzymology 289).

Within the scope of the invention are compositions comprised of polypeptides comprising different combinations of the various elements discussed above.

In one embodiment, $X_3$ is arginine and $X_4$ is phenylalanine. In this embodiment, the polypeptide contains the core fragment of arginine-tryptophan-glutamic acid-phenylalanine, the same consensus sequence originally identified in Peptides 8 and 13 (SEQ ID NO 8, SEQ ID NO 13) (see e.g. Examples 1 and 2). In an alternative embodiment, the polypeptide contains the sequence of arginine-tryptophan-glutamic acid-tyrosine. Both of these sequences were shown to increase inhibitory activity of the various compositions (see e.g. Example 9). These several non-limiting examples list but two of many possible core fragments comprised within the compositions of the invention. Other alternatives also exist. For example, when $X_3$ is arginine and $X_4$ is tryptophan, the composition also exhibits complement inhibition activity (see e.g. Peptide 7).

The core fragments discussed above can be combined with differing combinations of the other elements. For example, in one embodiment, where both $X_2$ and $X_5$ are any of a multitude of amino acid residues, and $X_1$ and $X_6$ are both hydrogen atoms, the polypeptide of the composition is a 6-mer. In a further embodiment of this 6-mer, $X_2$ is a hydrophobic amino acid. Experiments have demonstrated that a hydrophobic residue in the $X_2$ position increases activity (see e.g. Example 10, Example 15). Thus, this embodiment combines the benefits of the consensus sequence with that of a hydrophobic residue at $X_2$. In yet another embodiment of this 6-mer, $X_2$ is either tryptophan, tyrosine, valine, threonine, isoleucine, alanine, glutamic acid, threonine, or leucine, each of which showed further increases in complement inhibitory activity.

In another embodiment, the polypeptide is a 7-mer, similar in character to the above described 6-mer, but with either $X_1$ or $X_6$ being an amino acid residue. In another embodiment of this 7-mer, $X_1$ is an amino acid and this amino acid is either glutamic acid, aspartic acid, isoleucine, leucine, proline, or threonine. In a further embodiment of this 7-mer, $X_1$ is glutamic acid. Each of these embodiments showed increased complement inhibition (see e.g. Example 11, Example 15).

In a further embodiment of this 7-mer, $X_6$ is a bond linking the polypeptide to another component of the composition. In one embodiment, this component is a fusion construct of the polypeptide to another protein that functions to target the composition to specific tissues or cell types undergoing complement activation or complement over activation. In another embodiment, the polypeptide is pegylated, thereby increasing the in vivo half life of the composition by increasing molecular size. In a further embodiment, the polypeptide is glycosylated, thereby improving intestinal absorption of the composition. In still further embodiments, other components as discussed previously are attached to the 7-mer. Of course, each of these iterations can be reflected at $X_1$ when $X_6$ is an amino acid. Likewise, these same permutations could be present on $X_1$ or $X_6$ when the other is a hydrogen and the polypeptide is thus a 6-mer. The discussion of the 6-mer above applies here, in the context of coupling components to the polypeptide.

In another embodiment, the polypeptide is comprised of the optimal consensus sequence (as discussed previously), $X_2$ is either tryptophan, tyrosine, valine, threonine, isoleucine, or alanine amino acid residues, and both $X_1$ and $X_6$ are amino acid residues, thus forming an 8-mer. In a further embodiment of this 8-mer, $X_1$ is either glutamic acid, aspartic acid, isoleucine, leucine, or proline. In a still further embodiment of this 8-mer, $X_1$ is glutamic acid. Each of these variations have shown through experimentation to increase the complement inhibition activity of the composition.

It is apparent that additional amino acid residues may be present between $X_1$ and any other component associated with the polypeptide sequence of the invention, as well as between $X_6$ and any other component associated with the polypeptide sequence of the invention. Likewise, components (such as those discussed throughout the application) may be attached to $X_1$ and/or $X_6$, including when these residues are an amino acid(s). Similarly, additional amino acid residues may be present between $X_1$ and such components, as well as between $X_6$ and such components, both as to the 8-mer discussed here, and the 7-mer and 6-mer as discussed previously. In one embodiment, the polypeptide has a total number of amino acid residues ranging from about 6 to about 50. For example, the polypeptide can be from 7 to about 30 residues in length. As another example, the polypeptide can be from 8 to about 15 residues in length.

In each of the various embodiments listed above in which there is a modifiable terminal amino acid, a further embodiment exists wherein the polypeptide has an amino-terminal acetyl group. In each of the various embodiments listed above in which there is a modifiable carboxy-terminal amino acid, a further embodiment exists wherein the polypeptide has a carboxy-terminal amide group. And further, in each of the various embodiments listed above in which there is a modifiable amino-terminal amino acid and a modifiable carboxy-terminal amino acid, a further embodiment exists wherein the polypeptide has both an amino-terminal acetyl group and a carboxy-terminal amide group. In various embodiments, the terminal amino acid modified with a blocking group can be: $X_1$, $X_2$, $X_5$, $X_6$, or attached to $X_1$ or $X_6$, or an amino acid upstream or downstream from $X_1$ and/or $X_6$. Experiments have demonstrated that blocking the N-terminus (by acetylation) and the C-terminus (by amidation) of a polypeptide increased the inhibitory activity of this polypeptide, as measured by an RBC hemolysis assay (see e.g. Example 3, FIG. 7, FIG. 10).

In one embodiment, the polypeptide is comprised of an amino acid sequence(s) selected from the group consisting of SEQ ID NO 7, SEQ ID NO 8, SEQ ID NO 13, SEQ ID NO 46, SEQ ID NO 50, SEQ ID NO 65, SEQ ID NO 66, SEQ ID NO 69, SEQ ID NO 73, SEQ ID NO 74, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 103, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, and SEQ ID NO 121.

As an example, the polypeptide can be comprised of amino acid sequence(s) selected from the group consisting of SEQ ID NO 46, SEQ ID NO 50, SEQ ID NO 66, SEQ ID NO 73, SEQ ID NO 74, SEQ ID NO 76, SEQ ID NO 78, SEQ ID NO 80, SEQ ID NO 81, SEQ ID NO 82, SEQ ID NO 83, SEQ ID NO 84, SEQ ID NO 90, SEQ ID NO 91, SEQ ID NO 93, SEQ ID NO 95, SEQ ID NO 107, SEQ ID NO 109, SEQ ID NO 112, SEQ ID NO 113, SEQ ID NO 115, SEQ ID NO 117, SEQ ID NO 119, and SEQ ID NO 120.

As a further example, the polypeptide can be comprised of amino acid sequence(s) selected from the group consisting of SEQ ID NO 73, SEQ ID NO 80, SEQ ID NO 81, SEQ ID NO 82, SEQ ID NO 83, SEQ ID NO 84, SEQ ID NO 90, SEQ ID NO 91, SEQ ID NO 93, SEQ ID NO 95, SEQ ID NO 107, SEQ ID NO 109, SEQ ID NO 112, SEQ ID NO 115, SEQ ID NO 117, SEQ ID NO 119, and SEQ ID NO 120. As yet another example, the polypeptide can be comprised of amino acid sequence(s) selected from the group consisting of SEQ ID NO 112, 115, 117, and 120. In still another example, the polypeptide can be comprised of the amino acid sequence of SEQ ID NO 112.

In a further embodiment, the polypeptide is a truncated polypeptide formed from removal of residues from the amino terminus, carboxy terminus, or both termini of the sequences listed above. For example, Peptide 50 (SEQ ID NO 50), an 8-mer, was formed from truncation of Peptide 13 (SEQ ID NO 13), a 12-mer and retained full complement inhibition activity (see e.g. FIG. 6). Truncation methodology is well known in the art (Fields (1997) Methods in Enzymology 289). It is within the scope of the invention to truncate, for example, a 12-mer polypeptide to an 11-mer, 10-mer, 9-mer, 8-mer, 7-mer, or 6. Similarly, it is within the scope of the invention, for example, to truncate a 11-mer to a 10-mer, 9-mer, 8-mer, 7-mer, or 6-mer. Likewise, it is within the scope of the invention, for example, to truncate a 10-mer polypeptide to a 9-mer, 8-mer, 7-mer, or 6-mer. It is also within the scope of the invention, for example, to truncate a 9-mer polypeptide to an 8-mer, 7-mer, or 6-mer. In keeping with the previous examples, it is also within the invention, for example, to truncate an 8-mer to a 7-mer or 6-mer. Also, the truncation of a 7-mer to a 6-mer, for example, is within the scope of the invention. As these examples have illustrated, it is contemplated that specific polypeptides identified herein (e.g. SEQ ID NO 7, SEQ ID NO 8, SEQ ID NO 13, SEQ ID NO 46, SEQ ID NO 50, SEQ ID NO 65, SEQ ID NO 66, SEQ ID NO 69, SEQ ID NO 73, SEQ ID NO 74, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, and/or SEQ ID NO 97) may be truncated and these fragments used in various compositions of the invention either as solitary peptides, in conjunction with other polypeptides and/or fragments, and/or in association with any and all components and/or pharmaceutically acceptable vehicle(s) discussed herein.

Similarly, it is within the scope of the invention that polypeptides and fragments of polypeptides of the invention can be attached to additional amino acid residues, inserted into other polypeptide sequences, or embedded into other biomolecules.

The present invention also encompasses a polypeptide with twin cysteine residues that specifically binds C5, thereby inhibiting formation of C5b-9 (i.e., MAC) and concurrently elevating the level of C5a with some specificity for the classical complement pathway. In these compositions, the polypeptide comprises a sequence of $Z_1$-$C_1$-$Z_2$-P-$Z_3$-$Z_4$-$C_2$-$Z_5$.

In one composition of the invention, $Z_1$ can be a hydrogen atom or an amino acid residue. In one embodiment, $Z_1$ is a hydrogen atom. This hydrogen atom is attached to the terminal amino group of $C_1$. In this embodiment, the amino-terminus of the polypeptide sequence of the composition is the cysteine residue of $C_1$. In another embodiment, $Z_1$ is an amino acid residue, which can include natural and non-natural amino acids, analogs, and derivatives, as discussed previously. It is apparent that additional amino acid residues may be present between $Z_1$ and any other component associated with the polypeptide sequence of the invention.

In another composition of the invention, $Z_1$ can be a hydrogen atom, an amino acid residue, or a covalent bond linking the polypeptide to another component of the composition. In one embodiment, $Z_1$ is a hydrogen atom. This hydrogen atom is attached to the terminal amino group of $C_1$. In this embodiment, the amino-terminus of the polypeptide sequence of the composition is the cysteine residue of $C_1$. In another embodiment, $Z_1$ is an amino acid residue, which can include natural and non-natural amino acids, analogs, and derivatives, as discussed previously. It is apparent that additional amino acid residues may be present between $Z_1$ and any other component associated with the polypeptide sequence of the invention. In a further embodiment, $Z_1$ is a covalent bond linking the polypeptide to another component of the composition. Such coupled components, their functions, and methods of linkage are as discussed previously.

In keeping with traditional amino acid nomenclature, $C_1$ in the sequence above represents a cysteine residue. In one embodiment, $C_1$ and $C_2$ form a disulfide bridge and the conformation of the polypeptide is cyclized.

In exploring the role of the cysteine residues, $C_1$ and $C_2$ were reduced and alkylated, and the activity of the resulting polypeptide was tested via hemolysis assay (see e.g. Example 3 and Example 12). Reduction and alkylation of sulfhydryl groups is well known in the art (see e.g. Fields (1997) Methods in Enzymology 289). Results showed that complement-related activity of Peptide 6 (SEQ ID NO 6) was lost when $C_1$ and $C_2$ were reduced or alkylated (see e.g. Example 12). In various embodiments, the cysteine-containing peptide of the invention contains two cysteines linked via a disulfhydryl bridge. Cyclic peptides, such as the cysteine-bridged form of the peptide, are known to be highly permeable across the cellular barrier (see Pauletti 1997, at 242).

In several compositions there exists an embodiment where $Z_2$ is at least one amino acid residue. These amino acid residues can include a multitude of combinations of natural and non-natural amino acids, analogs, and derivatives, as discussed previously. In one embodiment, $Z_2$ is two amino acid residues. These two amino acid residues can include a multitude of combinations of natural and non-natural amino acids, analogs, and derivatives, as discussed previously.

In keeping with traditional amino acid nomenclature, P in the sequence above represents a proline residue. Alanine scanning and subsequent hemolysis assay (see e.g. Example 13) was used to discern particular residues in the polypeptide (see e.g. Peptide 6, SEQ ID NO 6) that contributed to its activity. Results showed that substitution of alanine residues for the P residue of Peptide 6 resulted in the loss of activity.

Alanine scanning was used to discern particular residues in the cyclized peptide (see e.g. Peptide 6, SEQ ID NO 6) that contributed to its activity. This method, well known in the art (Morison and Weiss (2001) Current Opinions in Chemical Biology 5:302-307; Cunningham and Wells (1989) Science 244:1081-1085), involved substituting an alanine residue at each position in a sequence and testing the resulting peptide derivative for activity. Loss of activity suggested that particular residue in the parent peptide plays a role in the function of the molecule. Various peptides were synthesized with an alanine residue substituted at each position of the sequence of Peptide 6 (SEQ ID NO 6). These peptides were tested in a classical hemolysis assay (see e.g. Example 3).

In several compositions of the invention, there exists an embodiment where $Z_3$ is a residue of a hydrophobic amino acid. Hydrophobic amino acids are those amino acids which have nonpolar side chains, and include the natural amino acid residues of valine, leucine, isoleucine, cysteine and methionine, as well as those hydrophobic amino acids with aromatic side chains, which include phenylalanine, tyrosine, and tryptophan.

In another embodiment, $Z_3$ is a residue of an aromatic amino acid. As discussed above, aromatic amino acids include phenylalanine, tyrosine, and tryptophan. In a further embodiment, $Z_3$ is a tryptophan residue. Results from alanine scanning experiments showed that substitution of an alanine residue for a $Z_3$ tryptophan residue in the above sequence resulted in the loss of activity (see e.g. Example 13).

In several compositions there exists an embodiment where $Z_4$ is at least one amino acid residue. These amino acid residues can include a multitude of combinations of natural and non-natural amino acids, analogs, and derivatives, as discussed previously. In one embodiment, $Z_1$ is a single amino acid residue, which can include natural and non-natural amino acid residues, analogs, and derivatives, as discussed previously.

In keeping with traditional amino acid nomenclature, $C_2$ in the sequence above represents a cysteine residue. In one embodiment, $C_1$ and $C_2$ form a disulfide bridge and the conformation of the polypeptide is cyclized.

In exploring the role of the cysteine residues, $C_1$ and $C_2$ were reduced and alkylated, and the activity of the resulting polypeptide was tested via hemolysis assay (see e.g. Example 3 and Example 12). Reduction and alkylation of sulfhydryl groups is well known in the art (see e.g. Gregg Fields (1997) Methods in Enzymology 289). Results showed that complement-related activity of Peptide 6 (SEQ ID NO 6) was lost when $C_1$ and $C_2$ were reduced or alkylated (see e.g. Example 12).

In one composition of the invention, $Z_5$ can represent either a hydrogen atom or an amino acid residue. In one embodiment, $Z_5$ is a hydrogen atom. This hydrogen atom is attached to the terminal amino group of $C_2$. In this embodiment, the carboxy-terminus of the polypeptide sequence of the composition is the cysteine residue of $C_2$. In another embodiment, $Z_5$ is an amino acid residue, which can include natural and non-natural amino acids, analogs, and derivatives, as discussed previously. It is apparent that additional amino acid residues may be present between $Z_5$ and any other component associated with the polypeptide sequence of the invention.

In another composition of the invention, $Z_5$ can represent either a hydrogen atom, an amino acid residue, or a covalent bond linking the polypeptide to another component of the composition. In one embodiment, $Z_5$ is a hydrogen atom. This hydrogen atom is attached to the terminal amino group of $C_2$. In this embodiment, the carboxy-terminus of the polypeptide sequence of the composition is the cysteine residue of $C_2$. In another embodiment, $Z_5$ is an amino acid residue, which can include natural and non-natural amino acids, analogs, and derivatives, as discussed previously. In a further embodiment, $Z_5$ is a covalent bond linking the polypeptide to another component of the composition. Such coupled components, their functions, and methods of linkage are as discussed previously.

It is apparent that additional amino acid residues may be present between $Z_5$ and any other component associated with the polypeptide sequence of the invention.

Prior discussion of differing combinations of elements, in the context of the X peptides, analogously applies to the Z peptide as well.

In one embodiment, the cysteine-containing polypeptide is comprised of amino acid residues in the sequence of SEQ ID NO 6. Previous discussion of truncation, in the context of the X peptide, analogously applies to the this series of peptides as well.

When the classical complement pathway was activated (via incubating an immune complex coated plate surface with plasma in the presence and absence of peptide), Peptide 6 (SEQ ID NO 6) inhibited the production of SC5b-9, but enhanced production of C5a. In contrast, when the alternate complement pathway was activated with the presence of zymosan or cellulose acetated hemodialysis membrane (both being alternative pathway activators), Peptide 6 (SEQ ID NO 6) inhibited production of SC5b-9 but had no effect on levels of C5a. Thus, the elevation of C5a levels by Peptide 6 is at least partially specific for the classical complement pathway's C5 convertase.

In one embodiment, each polypeptide or polypeptides of the composition of the invention comprises between about six to about fifty amino acid residues. In another embodiment, there are between about seven to about thirty amino acid residues. In yet another embodiment, there are between about eight to about fifteen amino acid residues. In a further embodiment, there are about twelve amino acid residues.

To evaluate the effect of peptide length on inhibitory activity of polypeptides, a series of truncated peptides were synthesized based on the structure of Peptide 13 (SEQ ID NO 13) and assayed with the RBC hemolysis assay (see e.g. Example 8). Results showed that removing amino acids sequentially from the amino terminus results in diminishing inhibitory activity. In contrast, removing the two residues from the carboxyl terminus appears to increase the activity of this peptide (Peptide 46, SEQ ID NO 46), which was reduced from twelve to ten amino acids. Furthermore, removing two amino acids from both ends of Peptide 13, generates an eight-mer (Peptide 50, SEQ ID NO 50) that retains all original activity. This same peptide showed further increases of complement inhibition from blocking the N-terminus (by acetylation) and the C-terminus (by amidation) as discussed previously.

To evaluate the effect of peptide length on inhibitory activity of cyclized polypeptides, a series of truncated peptides were synthesized based on the structure of Peptide 6 (SEQ ID NO 6) (see e.g. Example 14). Results showed that polypeptides with cysteine residues on both the amino- and carboxy-terminus retained activity. Results also indicated that activity of the cyclized peptide was enhanced as more amino acid residues were added to the ends.

The peptides of the current invention could be identified in a variety of ways. In one embodiment of the invention, a phage displayed peptide library was screened against C5 to look for a novel small molecule which could inhibit the proteolysis of C5 (see Example 1). Phage display describes a selection technique in which a peptide or protein is expressed as a fusion with a coat protein of a bacteriophage, resulting in display of the fused protein on the exterior surface of the phage virion, while the DNA encoding the fusion resides within the virion. Phage display can be used to create a physical linkage between a vast library of random peptide sequences to the DNA encoding each sequence, allowing rapid identification of peptide ligands for a variety of target molecules (antibodies, enzymes, cell-surface receptors, etc.) by an in vitro selection process called "panning." In its simplest form, panning is carried out by incubating a library of phage-displayed peptides with a plate (or bead) coated with the target, washing away the unbound phage, and eluting the specifically-bound phage. (Alternatively the phage can be reacted with the target in solution, followed by affinity capture of the phage-target complexes onto a plate or bead that specifically binds the target.) The eluted phage is then amplified and taken through additional cycles of panning and amplification to successively enrich the pool of phage in favor of the tightest binding sequences. After several rounds, individual clones are characterized by DNA sequencing and ELISA.

In the current invention, screening of the phage library against C5 could be performed by several different methods which include, but are not limited to: directly coating a surface with the target protein and then screening with the library; screening against biotinylated C5 immobilized on a neutravidin coated surface; or screening against C5a, the small fragment after proteolysis of C5 to determine if a site may be available on that fragment which is also present in C5 and prevents cleavage of native C5. One of many possible methodologies suitable for phage display identification of complement inhibitors is detailed in Example 1.

From the panning described above, four peptides (Peptide 6, SEQ ID NO 6; Peptide 7, SEQ ID NO 7; Peptide 8, SEQ ID NO 8; and Peptide 13, SEQ ID NO 13) showed both specific binding to C5 and inhibition of the classical pathway hemolysis assay, indicating inhibition of complement activity. Three of these peptides (Peptides 7, 8, and 13) contained a four-amino acid consensus sequence of arginine, tryptophan, glutamic acid, and, lastly, tryptophan or phenylalanine. Competition assays with phage bound peptide clones and free synthetic peptides demonstrated that consensus sequence peptides all competed with each other for binding C5 (see e.g. Example 2). Also isolated was a fourth peptide (Peptide 6, ID SEQ NO 6), having two cysteine residues, that showed both specific binding to C5 and inhibition of the classical pathway hemolysis assay.

To further elucidate the inhibitor effects upon the specific steps of the cascade, the generation of complement activation products C5a, C5b-9, and C3a was monitored upon activation of the cascade by the classical pathway (see e.g. Example 4), alternative pathway (see e.g. Example 5), and a combination of pathways (see e.g. Example 6).

Peptides 8 (SEQ ID NO 8) and 13 (SEQ ID NO 13) were demonstrated to behave in a similar manner in all three of the modes of activation. Both peptides displayed dose dependent inhibition of both C5a and SC5b-9 generation when activated by either the classical or alternative pathways, indicating these peptides inhibit the conversion of C5 into C5a and C5b. Although the mechanism is not clearly defined, the peptide does bind C5 and affects subsequent interaction with other complement proteins. As proposed mechanisms, the peptide could be specifically binding to the site on C5 which normally binds the convertase and therefore sterically blocks the convertase from binding, or it could bind at another site and cause a conformational change in C5 which inhibits or changes the binding of C5 to the convertase. It has recently been reported that the rC345C module of C5, a 150 residue C-terminal extension of the α-subunit harboring three internal disulfide bonds, is responsible for binding converatse, C6, and C7 (Thai & Ogata (2003) J. Immuno. 171:6565-6573). These are only proposed mechanisms and do not serve to limit in any way the invention to any particular mechanism. Neither of these two peptides have any effect on the production of C3a. Neither of these peptides demonstrated specificity for either the classical or the alternate complement activation pathway.

Peptide 7 (SEQ ID NO 7) behaved similar to peptide 8 (SEQ ID NO 8) and 13 (SEQ ID NO 13) in its inhibition of C5a and SC5b-9. One difference between peptide 7 and peptides 8 and 13 is the observed dose dependent increase or activation of C3a production. While the other two peptides show little to no effect on C3a production, peptide 7 promotes an enhanced production of C3a levels. Given that C3 and C5 are approximately 70% homologous, there may be cross-reactivity with C3 in the case of peptide 7. It is foreseeable that dual activity (inhibition of C5 proteolysis and activation of C3 proteolysis) will be clinically useful stemming from concurrent lowering of inflammation response and other C5-mediated damaging effects and increases in C3-mediated immunosurveillance functions.

Peptide 6 (SEQ ID NO 6) behaved differently from the other three identified peptides in that Peptide 6 inhibited the production of SC5b-9, but elevated levels of C5a in certain pathways. Both of these effects were demonstrated to be dose dependent. The C5a-elevation effect of Peptide 6 was shown to be specific for the classical complement activation pathway. Similar to Peptides 8 and 13, Peptide 6 had no effect on the production of C3a.

Though the peptide encoded by SEQ ID NO 6 binds to C5 and inhibits production of the membrane attack complex, results suggest a different mechanism of inhibition for this peptide, consistent with the evidence that it binds to C5 at a site unique to that of the other peptides. Peptide 6 may induce a conformational change such that it alters the interaction with the classical pathway convertase (C3bC4bC2b), but not with the alternative pathway convertase (C3bC3bBb). In fact, peptide 6 may actually increase C5 conversion by the classical pathway convertase complex. In addition, peptide 6 may bind to C5 at a site that blocks the formation of terminal complex either through a conformational change or sterically blocking the binding site for C6 and/or C7.

Recent work by several investigators have begun to define the binding sites on C5 and C5b that interact with the C5 convertase enzymes and the terminal components, C6 and C7. A region at the carboxyl-terminus of the alpha chain, comprising the last 146 residues, appears to be involved in both the interaction of C5 with the converatase enzymes as well as the binding of C5b to both C6 and C7. This suggests that peptides 6 and 7/8/13 may bind to sites located in or near this same region of the C5 protein.

The peptide components of the current invention could be made in many ways. For instance, synthesis of the peptides and mimetics of the present invention may be accomplished using known peptide synthesis techniques. The peptides and mimetics may be synthesized on a solid support (such as polystyrene utilizing 4 as a linker) by techniques well known in the art (see e.g., Fields (1997) Methods in Enzymology 289, Stewart & Young (1984) Solid Phase Peptide Synthesis, Pierce Chemical Comp., Rockford, Ill.; Atherton & Shepard (1989) Solid Phase Peptide Synthesis: A Practical Approach, Oxford). For example, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses. In another embodiment, the peptides of the present invention can be produced by classical solution peptide synthesis, also known as liquid-phase peptide synthesis. Polypeptides are also available commercially from, e.g., Sigma Chemical Co. (St. Louis, Mo.), Bachem Bioscience, Inc. (King Of Prussia, Pa.), and Peptides International (Louisville, Ky.).

In addition, the DNA sequences encoding the peptides or fragments, analogs or variants thereof can be produced by synthetic methods. The synthesis of nucleic acids is well known in the art. See e.g., Brown et al. (1979) Methods in Enzymology, 68:109-151. The DNA segments corresponding to the amino acid sequences described herein can be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See e.g., Oligonucleotide Synthesis, a Practical Approach (M. J. Gait, ed., 1984).

Following the synthesis of DNA sequences, such sequences are produced by utilizing recombinant systems. The basic steps in the recombinant production of desired peptides are: a) construction of a synthetic or semi-synthetic DNA encoding the peptide of interest; b) integrating said DNA into an expression vector in a manner suitable for the expression of the peptide of interest, either alone or as a fusion protein; c) transforming an appropriate eukaryotic or prokaryotic host cell with said expression vector, d) culturing said transformed or transfected host cell in a manner to express the peptide of interest; and e) recovering and purifying the recombinantly produced peptide of interest.

The methods of recombinantly producing peptides/proteins are well known in the art. Literature that describes these techniques includes, for example, Sambrook, et al., Molecular Cloning: A Laboratory Manual, Cold Spring Harbor Laboratory, Cold Spring Harbor, N.Y. (2nd edition, 1989); Ausubel et al. (1987) Current Protocols in Molecular Biology; O'Reilly, et al. (1992) Baculovirus Expression Vectors: A Laboratory Manual; Practical Molecular Virology (Collins, ed., 1991); Culture of Animal Cells: A Manual of Basic Technique (Freshney, ed., 2nd edition, 1989); J. Miller (1972) Experiments in Molecular Genetics, Cold Spring Harbor Laboratory, Cold Spring Harbor, N.Y.; Morrison (1979) Transformation and Preservation of Competent Bacterial Cells by Freezing, Methods Enzymol. 68:326-331; and Perbal (1984) A Practical Guide to Molecular Cloning, John Wiley & Sons.

After the desired peptide is obtained either by chemical synthesis or recombinant methods, it can be isolated and purified using a number of procedures that are well known in the art, such as, e.g., extraction, precipitation, chromatography, affinity chromatography, electrophoresis, or the like.

Within the scope of the present invention are polypeptide analogs of the invention arrived at by amino acid substitutions. One factor that can be considered in making amino acid substitutions is the hydropathic index of amino acids. The importance of the hydropathic amino acid index in conferring interactive biological function on a protein has been discussed by Kyte and Doolittle ((1982) J. Mol. Biol., 157: 105-132). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within 2 are substituted for one another. More preferred substitutions are those wherein the amino acids have hydropathic indices within 1. Most preferred substitutions are those wherein the amino acids have hydropathic indices within 0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0+/−1); serine (+0.3); asparagine/glutamine (+0.2); glycine (0); threonine (−0.4); proline (−0.5+/−1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within 2 are preferably substituted for one another, those within 1 are more preferred, and those within 0.5 are most preferred.

As outlined above, amino acid substitutions in the peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences.

It will be appreciated by those of skill in the art that a peptide mimic may serve equally well as a peptide for the purpose of providing the specific backbone conformation and side chain functionalities required for binding to C5 and inhibiting complement activation. Accordingly, it is contemplated as being within the scope of the present invention to produce C5-binding, complement-inhibiting compounds through the use of either naturally-occurring amino acids, amino acid derivatives, analogs or non-amino acid molecules (as discussed previously) capable of being joined to form the appropriate backbone conformation. A non-peptide analog, or an analog comprising peptide and non-peptide components, is sometimes referred to herein as a "mimetic" or "peptidomimetic," to designate substitutions or derivations of the peptides of the invention, which possess the same backbone conformational features and/or other functionalities, so as to be sufficiently similar to the exemplified peptides to inhibit complement activation. The use of peptidomimetics for the development of high-affinity peptide analogs is well known in the art (see e.g., Zhao et al. (1995) Nature Structural Biology 2:1131-1137; Beely (1994) Trends in Biotechnology 12:213-216; Hruby (1993) Biopolymers 33:1073-1082).

The present invention is also applicable to the use of the compositions discussed above to inhibit complement in a clinical setting. The C5-targeting activity of the composition of the invention can function to inhibit complement activation and inflammatory manifestations that accompany it, such as recruitment and activation of macrophages, neutrophils, platelets, mast cells and endothelial cells, edema, and tissue damage. Thus, the composition of the invention can be used to treat any condition or disease where C5 proteolysis contributes to the condition or disease. Such conditions and diseases generally include autoimmune diseases, ischemia/reperfusion settings, neurologic disease, infectious disease, pulmonary settings, and other settings. Examples of autoimmune diseases include rheumatoid arthritis, type II collagen-induced arthritis, systemic lupus erythamatosis, psoriasis, myasthenia gravis, Hashimoto's thyroiditis, inflammatory bowel disease (Crohn's disease), glomerulonephritis, immune-complex-induced vasculitis, and anti-phosolipid syndrome (recurrent miscarriage). Examples of ischemia/reperfusion settings include cardiopulmonary bypass graft surgery, myocardial infarction, stroke, atherosclerosis/vasculitis, renal ischemia/reperfusion, angioplasty, and trauma. Examples of neurologic, i.e. central nervous system, disease include Alzheimers, Multiple Sclerosis, and Parkinson's Disease. Examples of infectious disease include systemic inflammatory response syndrome (SIRS), sepsis, adult respiratory distress syndrome (ARDS), and recurrent infections. Examples of pulmonary settings include asthma, idiopathic pulmonary fibrosis, adult respiratory distress syndrome, and chronic obstructive pulmonary disease (COPD). Examples of other settings include diabetes, inflammation resulting from extracorporeal dialysis and blood oxygenation, chronic kidney disease, transplantation rejection, hyperacute allograft and hyperacute xenograft rejection, hereditary angioedema, experimental allergic neuritis, hemolytic anemia, thermal injury (e.g., burn and frostbite), proximal nocturnal hemoglobinuria, intestinal inflammation of Crohn's disease which is characterized by the lymphoid infiltration of mononuclear and polymorphonuclear leukocytes, toxicity and side effects observed from recombinant IL-2 immunotherapy treatment, and complement activation known to occur in monoclonal antibody therapy.

For instance, the composition can be used to treat inflammation. "Treat" is used herein to mean that the inflammatory response is reduced or prevented. As noted above, inflammation in some diseases has been associated with the deposition of immune complexes in tissues and the activation of the complement cascade. The complement cascade, and the action of the complement components, alone or concurrently with other biologic molecules, ultimately leads to tissue damage. Accordingly, a composition of the invention comprising polypeptide or polypeptides, can be administered to a mammal suffering from inflammation mediated by the complement pathway to inhibit the formation of C5a and/or C5b-9, and, thereby reduce or prevent tissue damage and further inflammation. Inflammatory diseases that can be treated include, but are not limited to, autoimmune diseases. Also, the inflammation associated with bacterial or viral infections can be treated.

The compositions of the present invention will also find use in other situations in which inhibition of complement activation is desired. For instance, complement activation that occurs in xerographic or allographic transplant may be inhibited by administering a composition of the invention to a person or animal receiving such transplant, or by coating organs, tissues, or cells with a composition of the invention. Further, the composition of the present invention can be used to coat biomaterials used in artificial organs, implants, and other medical devices, nonexclusive examples of which include stents, artificial hearts, pacemakers, valves, joints, catheters, membranes, or tubing, to inhibit complement activation which occurs during use of these artificial materials.

As an ex vivo example, complement activation during extracorporeal shunting of physiologic fluid may be inhibited by coating the tubing through which the fluids flow with a composition of the invention. This method can be applied to a variety of extracorporeal shunting techniques, including hemodialysis, kidney dialysis, and cardiopulmonary bypass circuits.

Effective dosage forms, modes of administration and dosage amounts of the composition of the invention may be determined empirically, and making such determinations is within the skill of the art. It is understood by those skilled in the art that the dosage amount will vary with the particular composition employed, the condition being treated, the severity of the condition, the route of administration, the rate of excretion, the duration of the treatment, the identity of any other drugs being administered to the mammal, the age, size and species of the mammal, and like factors well known in the medical and veterinary arts. In general, a suitable daily dose of a compound of the present invention will be that amount which is the lowest dose effective to produce a therapeutic effect. However, the total daily dose will be determined by an attending physician or veterinarian within the scope of sound medical judgment. If desired, the daily dose may be administered in multiple sub-doses, administered separately at appropriate intervals throughout the day.

The composition of this invention, including polypeptides, molecules, and fragments therein, can be administered to mammals in an appropriate pharmaceutical formulation by a variety of routes, including, but not limited to, pulmonary, intravenous infusion, intravenous bolus injection, and intraperitoneal, intradermal, intramuscular, subcutaneous, intratracheal, intraspinal, intracranial, topical (including ophthalmic, vaginal, rectal, intranasal, epidermal and transdermal) and oral routes. Such administration enables the composition to bind to endogenous C5 and thus inhibit C5 activation.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Formulations for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral administration may include sterile aqueous solutions which may also contain buffers, diluents and other suitable additives. Formulation of drugs is discussed in, for example, Hoover (1975) Remington's Pharmaceutical Sciences, Mack Publishing Co., Easton, Pa.; and Liberman & Lachman, Eds. (1980) Pharmaceutical Dosage Forms, Marcel Decker, New York, N.Y.

Regardless of the method by which the compositions of the invention are introduced into a patient, colloidal dispersion systems may be used as delivery vehicles to enhance the in vivo stability of the compositions and/or to target the compositions to a particular organ, tissue, or cell type. Colloidal dispersion systems include, but are not limited to, macromolecule complexes, nanocapsules, microspheres, beads and lipid-based systems including oil-in-water emulsions, micelles, mixed micelles, liposomes and lipid:composition complexes of uncharacterized structure.

The pharmaceutical compositions of the invention comprise a composition of the invention as an active ingredient in admixture with one or more pharmaceutically-acceptable vehicles and, optionally, with one or more other compounds, drugs, or other materials. Such vehicles are well known in the art, as are methods of preparing pharmaceutical compositions.

Pharmaceutical compositions of the invention suitable for administrations comprise one or more compositions of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient, or suspending or thickening agents. Pharmaceutically acceptable cations include metallic ions and organic ions. Metallic ions include, but are not limited to, appropriate alkali metal salts, alkaline earth metal salts and other physiologically acceptable metal ions. Exemplary ions include aluminum, calcium, lithium, magnesium, potassium, sodium and zinc in their usual valences. Organic ions include, but are not limited to, protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Examples of suitable aqueous and nonaqueous vehicles which may be employed include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption, such as aluminum monosterate and gelatin, or by dissolving or suspending the composition(s) in an oil vehicle.

The formulations may be presented in unit-dose or multi-dose sealed containers (for example, ampoules and vials). The formulations may be stored in a lyophilized condition requiring only the addition of the sterile liquid carrier, for example water for injection, immediately prior to use.

In certain embodiments, the pharmaceutical compositions described herein can be provided as prodrugs (see e.g. Pauletti et al. (1997) Adv. Drug Delivery Rev. 27:235-256). Prodrugs can be created, e.g., through the creation of a labile and reversible ester bond (see Wang et al., Curr. Pharm. Design 1999 5: 265-287). Such esterification can simultaneously mask the amino and carboxy groups, reduce intermolecular hydrogen-bonding potential, increase membrane permeability, and effect metabolic lability of the peptide (Wang et al. 1999, at 275). By way of example, esterification of any of the X1-9 can be used to create prodrugs. To achieve such esterification, the position is selected among X1-9 based on the presence of an amino acid that contains either an alcohol or acid (carboxyl) group. For example, when using a natural amino acid at any of these positions, which contains an alcohol group (such as serine, threonine, tyrosine or hydroxyproline or hydroxylysine, these amino acids can be modified with an acid (such as acetic acid) to create an ester. Conversely, aspartic acid and glutamic acid as well as the carboxyl terminus can be esterified with alcohols such as ethanol to make esters. Non-proteogenic or non-natural/synthetic amino acids that contain either an alcohol or carboxylic acid group can also be modified in this manner. Upon administration to a patient, the prodrugs created in this way are converted to active compounds upon either the hydrolysis of the ester bond by esterases or by the action of the acid in the stomach.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Panning Against C5

Peptides were identified by panning an M13 phage library (New England Biolabs), a random 12mer peptide library with a diversity of $10^{11}$ different peptide structures, against complement component C5. The phage library was panned against C5 using three different methods for immobilizing C5. The binding reactions all contained $2\times10^{11}$ phage particles in PBS containing 0.5% BSA and 0.3% Tween 20. The binding reactions were carried out at 25° C. for two hours and then unbound phage were removed by washing 5 times with PBS containing 0.5% BSA and 0.3% Tween20. The phage were eluted by acid (0.2 M Glycine pH 2.2, 1 mg/mL BSA) and immediately neutralized with 1 M Tris pH 9.1. Following elution, recovered phage were amplified in ER2738 E. coli (NEB) and subjected to two more rounds of panning as described above. The methods for immobilizing C5 include directly coating C5 (Advanced Research Technologies) to the surface (1 µg/mL), capturing biotinylated C5 (1 µg/mL) on a neutravidin (Pierce) coated surface, and capturing biotinylated C5a (1 µg/mL) on a neutravidin (Pierce) coated surface. C5 and C5a (Quidel) were biotinylated by incubating with 10 fold molar excess of Sulfo-NHS-LC-LC-Biotin for 2 hours at room temperature at pH 7.4 and then removing excess biotin by gel filtration. A negative selection was performed in the final round against neutravidin for the two latter screening methods. DNA from twenty randomly selected clones from each of the three final libraries was isolated and sequenced.

All of the peptide sequences which were determined at a frequency greater than one plus any sequence which contained a sequence of at least four amino acids which were homologous to another sequence were chosen to be synthesized as free peptides. These selected peptide sequences, identified as specifically binding to C5 and/or C5a, were synthesized and purified to greater than 90% purity by AnaSpec (San Jose, Calif.). Peptides were dissolved in either water or DMSO at concentrations of 10 mg/mL. Accordingly, all assays included controls to account for the effects of any DMSO added.

A consensus sequence of RWE(F/W) appeared in several of the peptides that specifically bound complement component C5 (Peptide 7, SEQ ID NO 7; Peptide 8, SEQ ID NO 8; and peptide 13, SEQ ID NO 13). These three C5-binding peptides were further shown to inhibit RBC hemolysis in a dose-dependent manner (see e.g. FIG. 1, FIG. 10). A fourth peptide (Peptide 6, SEQ ID NO 6) also specifically bound C5 and was later shown to inhibit RBC hemolysis in a dose-dependent manner (see e.g. FIG. 1).

Example 2

Phage Clone Binding to C5

The binding sites of the peptides were further probed via C5-binding competition assays. Increasing concentrations of each phage clone were incubated for 2 hours with 200 ng of biotinylated C5 in PBS containing 0.5% BSA. The phage bound C5 complex was captured on a neutravidin coated microplate for 20 minutes at room temperature and then washed with PBS containing 0.5% BSA. A peroxidase labeled anti-M13 antibody (Pharmacia) was used to detect the amount of phage bound to C5 with OPD substrate. Competition assays with free peptide were carried out in a similar manner except that one concentration of each phage clone was used which was determined as the concentration giving approximately 50% binding in the previous titration. Free peptide was added to the phage clones at concentrations of 50, 10 and 1 μM and incubated with the biotinylated C5 and the assay was carried out as above.

The binding assays showed all peptides bound C5. Furthermore, the binding assays showed significant competition among phage clones containing peptides with the RWE(F/W) consensus sequence (Peptide 7, SEQ ID NO 7; Peptide 8, SEQ ID NO 8; Peptide 13, SEQ ID NO 13), suggesting all such peptides bound to the same site on complement component C5. Results also indicated that Peptide 6 (SEQ ID NO 6) does not compete with the other three peptides, and hence, binds at a different site on C5.

Example 3

Classical Pathway Hemolytic Assay

Figure 10:
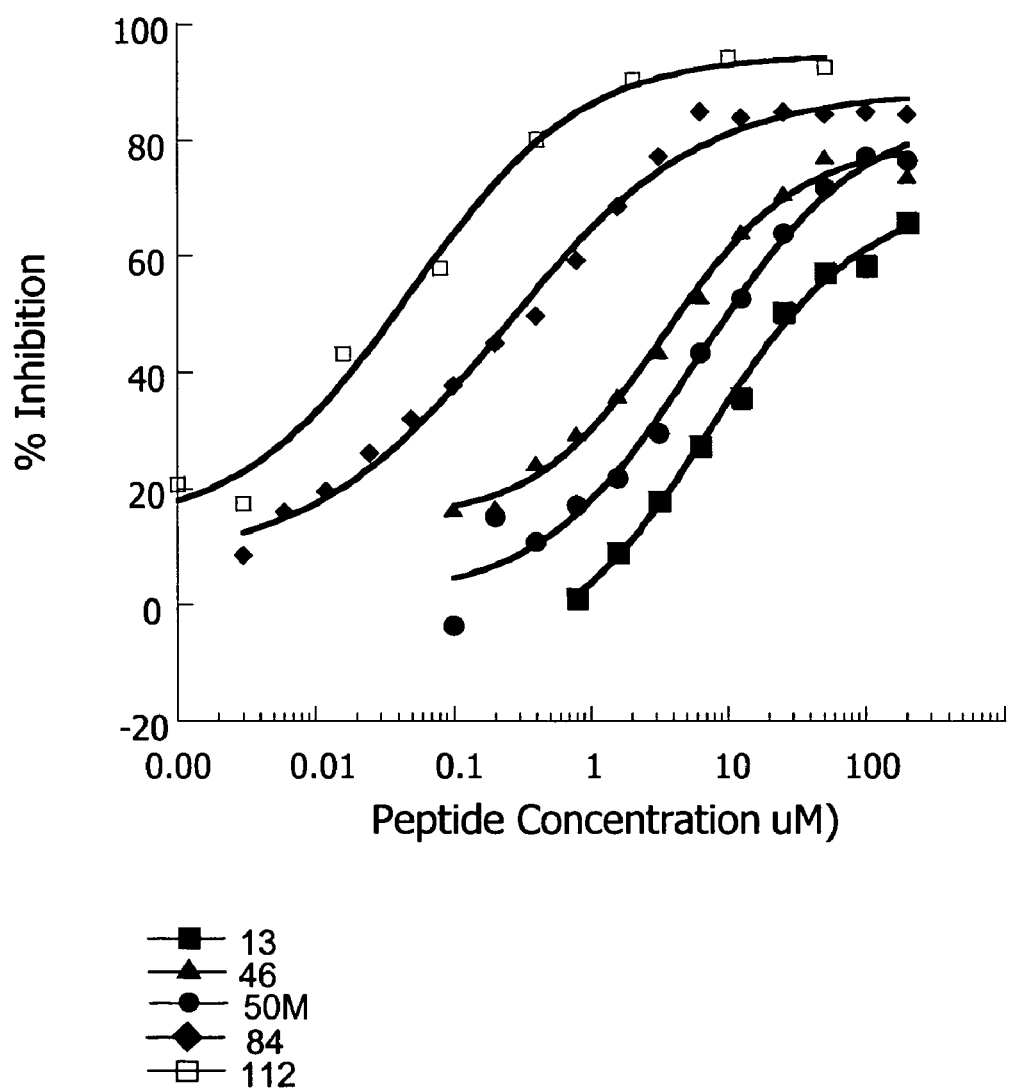
FIG. 10 is a line graph showing the dose dependent titration curve of percent inhibition of classical pathway hemolysis versus peptide concentration for peptides SEQ ID NOs 13, 46, 50M, 84, and 112. See Examples 3 and 11 for information regarding methodology.

Inhibition of the classical pathway by the peptides was measured using a standard hemolysis assay, which monitors the lysis of sheep erythrocytes as a result of terminal complex formation (see e.g. FIG. 1, FIG. 10). Various concentrations of peptide were incubated with 50 μL pooled human plasma (diluted 1:30 with GVB$^{++}$), 5×10$^7$ antibody sensitized sheep erythrocyte cells, and GVB$^{++}$ buffer to a final volume of 200 μL. The reaction was incubated at 37° C. for one hour and centrifuged. The percentage of lysis was determined by measuring the optical density of the supernatant at 414 nm. 100% lysis was determined by the optical density at 414 nm of the supernatant from a control sample consisting of 5×10$^7$ antibody sensitized sheep erythrocyte cells in water. The percent inhibition was calculated as the (% lysis$_{no\ peptide}$−% lysis$_{peptide}$)/% lysis$_{no\ peptide}$×100.

Results showed that, at 100 uM concentrations, several peptides (peptide 7, SEQ ID NO 7; Peptide 8, SEQ ID NO 8; and peptide 13, SEQ ID NO 13) demonstrated significant inhibition of hemolysis. Further experiments show that these peptides inhibit lysis in a dose dependent manner with IC$_{50}$ concentrations of 48.9 μM, 5.8 μM, and 29.2 μM, respectively (see e.g. FIG. 1). Results also showed that Peptide 6 (SEQ ID NO 6) significantly inhibited hemolysis in a dose dependent manner with IC$_{50}$ concentration of 3.0 μM.

Example 4

Classical Pathway Component Assay

Peptides were screened for their effect on complement activation to determine if the sites on C5 they were binding had an impact on activation of the cascade. The inhibition of the classical pathway by the peptides was measured by incubating human plasma in the presence and absence of peptides with an immune complex generated on a surface and then monitoring for the production of complement components C5a, SC5b-9, and C3a. To generate the immune complex, a 10 mg/mL solution of BSA in PBS was incubated at 56° C. for 30 minutes and then used to coat the surface of a microplate by diluting to 50 μg/mL at pH 9.6 and incubating for one hour at 37° C. The plate was washed and then incubated with 18 μg/mL mouse anti-BSA IgG2a (Sigma) for one hour at 37° C. Pooled human plasma with and without various concentrations of peptide were incubated for 30 minutes at 37° C. with the generated immune complex and the reaction was stopped with the addition of EDTA. The plasma samples were then analyzed with commercially available ELISA's for the production of C5a (Pharmingen), SC5b-9 (Quidel), and C3a (Quidel).

Figure 2A:
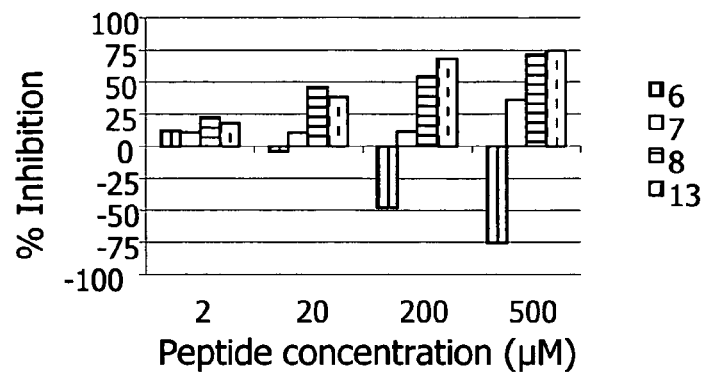
FIG. 2 is a series of bar graphs showing inhibition of complement activation when initiated by the classical pathway in the presence of an immune complex for peptides 6, 7, 8, and 13. Percent inhibition of the generation of complement components a.) C5a, b.) SC5b-9, and c.) C3a versus the peptide concentration are shown in the figure. See Example 4 for information regarding methodology.
Figure 2B:
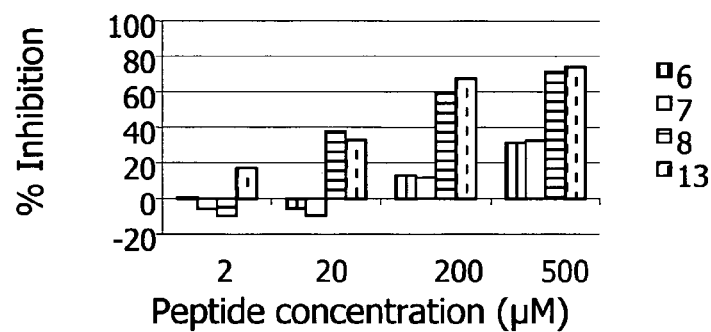

Results showed peptides having sequences of those in Peptide 8 (SEQ ID NO 8) and Peptide 13 (SEQ ID NO 13) behaved in a similar fashion, where both showed a dose-dependent increase in the inhibition of C5a and SC5b-9 production, indicating inhibition of the cleavage of C5 into C5a and C5b (see e.g. FIGS. 2a and 2b). In addition, neither of these peptides produced an effect on the production of C3a (see e.g. FIG. 2c).

Figure 2C:
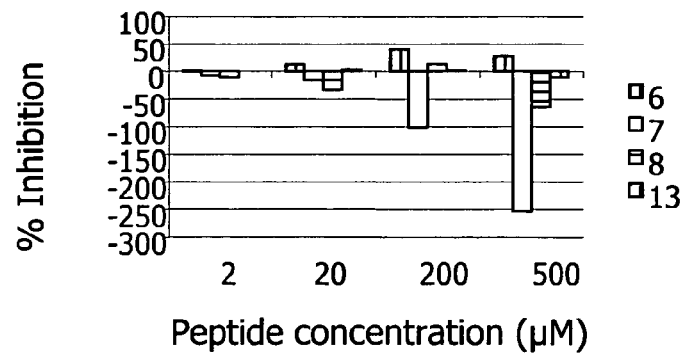

The results also showed that a peptide (Peptide 7, SEQ ID NO 7) inhibited C5a and SC5b-9 (see e.g. FIG. 2a and b) and enhanced production of C3a levels, particularly at high concentrations of peptide (see e.g. FIG. 2c). These effects were shown to be dose-dependent.

Results also showed that Peptide 6 (SEQ ID NO 6) inhibited SC5b-9 production (see e.g. FIG. 2b) but elevated levels of C5a (see e.g. FIG. 2a). These effects were shown to be dose-dependent. Peptide 6 showed no effect on C3a (see e.g. FIG. 2c).

Example 5

Alternative activation pathway C.A. Membrane Assay

Inhibition of the alternative pathway by the peptides was determined by incubating pooled human plasma in the presence and absence of various concentrations of peptide with 20 mg of cellulose acetate hemodialysis membrane at 37° C. for one hour. The reaction was stopped with EDTA and then the samples were analyzed with commercially available ELISA's for the production of C5a (Pharmingen), SC5b-9 (Quidel), and C3a (Quidel).

Figure 3A:
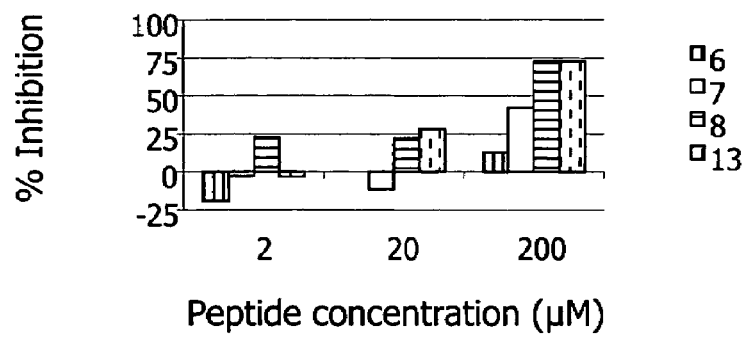
FIG. 3 is a series of bar graphs showing inhibition of complement activation initiated by the alternative pathway on cellulose acetate hemodialysis membranes for peptides 6, 7, 8, and 13. Percent inhibition of the generation of complement components a.) C5a, b.) SC5b-9, and c.) C3a versus the peptide concentration are shown in the figure. See Example 5 for information regarding methodology.
Figure 3B:
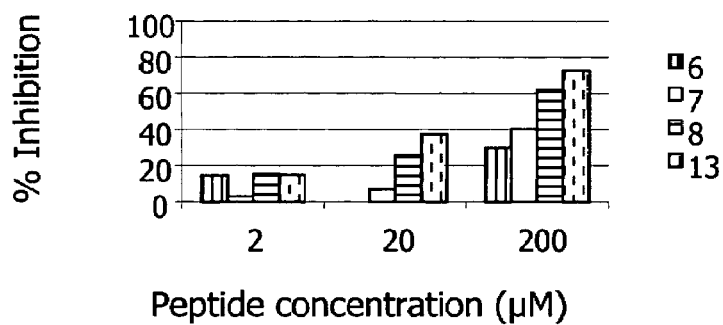
Figure 3C:
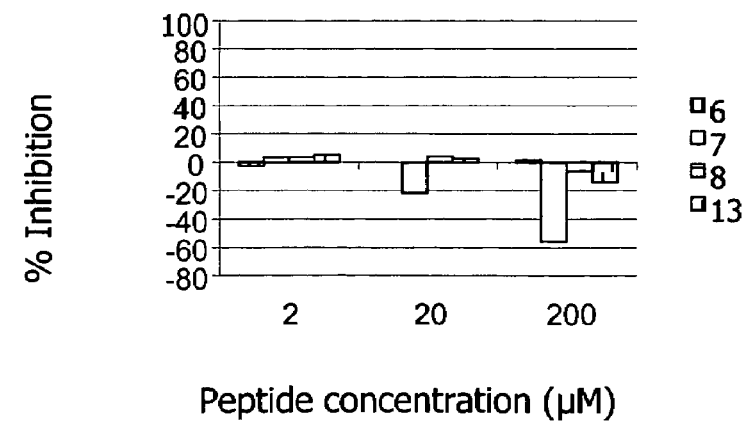

Results showed that, in this system, the peptides exhibited similar behavior as they did in the classical pathway system (see e.g. FIG. 3). Some peptides (Peptide 8, SEQ ID NO 8 and peptide 13, SEQ ID NO 13) showed dose-dependent inhibition of C5a and SC5b-9 generation with no effect on C3a production. Under alternate pathway activation, Peptide 7 (SEQ ID NO 7) inhibited C5a and SC5b-9 and also activated C3a generation. These effects were shown to be dose-dependent. Under alternate activation, Peptide 6 (SEQ ID NO 6) inhibited SC5b-9 production in a dose-dependent fashion (see e.g. FIG. 3b) but, in contrast to the classical pathway, had little effect upon C5a (see e.g. FIG. 3a). Neither did Peptide 6 show any effect on C3a (see e.g. FIG. 3c).

Example 6

Alternative Activation Pathway Zymosan Assay

The peptides were evaluated for involvement in activation of the complement system by the presence of zymosan. Zymosan, or yeast cell wall, has largely been described as an alternative pathway activator. In addition, there are sugars on the surface of the yeast cell wall which are capable of activating the lectin pathway. Therefore, zymosan can be considered as a general complement activator.

Varying concentrations of peptide were incubated with 2 mg/mL zymosan in pooled human plasma. The reactions were incubated at 37° C. for one hour and then stopped by the addition of EDTA. The samples were centrifuged, the plasma removed, and analyzed with commercially available ELISA's for the production of C5a (Pharmingen), SC5b-9 (Quidel), and C3a (Quidel).

Figure 4A:
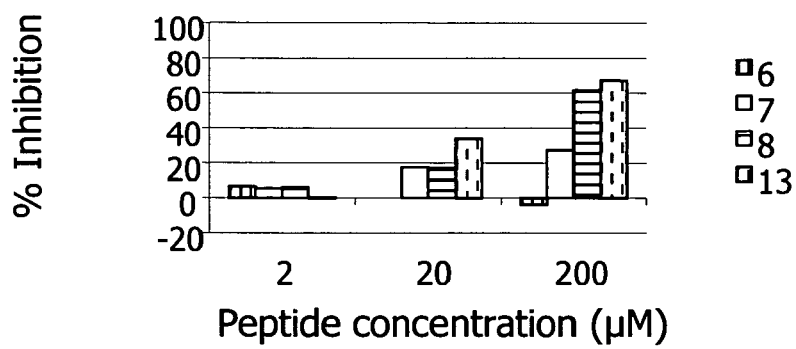
FIG. 4 is a series of bar graphs showing inhibition of complement activation in the presence of 2 mg/mL zymosan by peptides 6, 7, 8, and 13. Percent inhibition of the generation of complement components a.) C5a, b.) SC5b-9, and c.) C3a versus the peptide concentration are shown in the graph. See Example 6 for information regarding methodology.
Figure 4B:
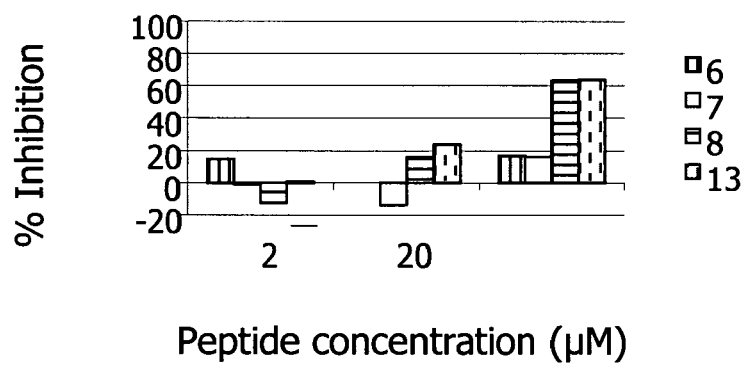
Figure 4C:
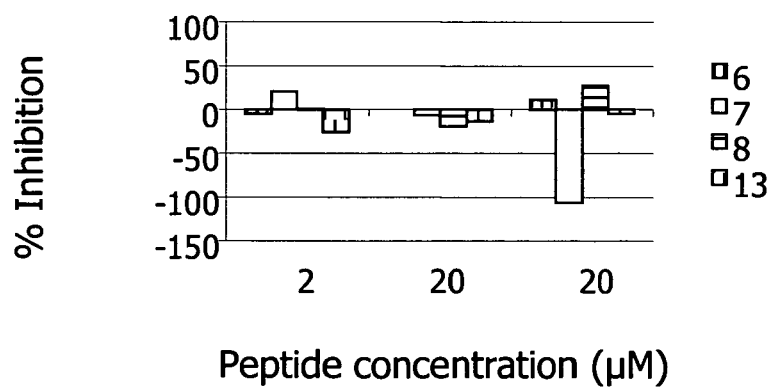

Results showed that Peptide 8 (SEQ ID NO 8) and Peptide 13 (SEQ ID NO 13) inhibited C5a and SC5b-9 production (in a dose-dependent fashion) with no observeable effect on C3a generation (see e.g. FIG. 4). Under zymosan activation of the alternate pathway, Peptide 7 (SEQ ID NO 7) inhibited C5a and SC5b-9 production and also activated C3a generation. These effects were shown to be dose-dependent. Under zymosan activation, Peptide 6 (SEQ ID NO 6) inhibited SC5b-9 production in a dose-dependent fashion (see e.g. FIG. 4b) but, in contrast to the classical pathway, had little effect upon C5a (see e.g. FIG. 4a). Neither did Peptide 6 show any effect on C3a (see e.g. FIG. 4c).

Example 7

Alanine Scan on C5-Binding Peptide

Alanine scanning was used to discern residues in the polypeptides that contribute to its activity. Alanine scanning methodology is well known in the art (Morison and Weiss (2001), Current Opinions in Chemical Biology 5:302-307; Cunningham and Wells (1989), Science 244:1081-1085), and involved substituting an alanine residue at each position in a sequence and testing the resulting peptide derivative for activity. Loss of activity suggests that particular residue in the parent peptide may play an important role in the function of the molecule. Peptide 7 (SEQ ID NO 7) was arbitrarily chosen for the analysis. The various peptides were synthesized with an alanine residue substituted at each position in the Peptide 7 (SEQ ID NO 7) sequence. These peptides were tested in an immune complex-classical pathway assay, measuring C5a and SC5b-9 production (see e.g. FIG. 5).

Figure 5:
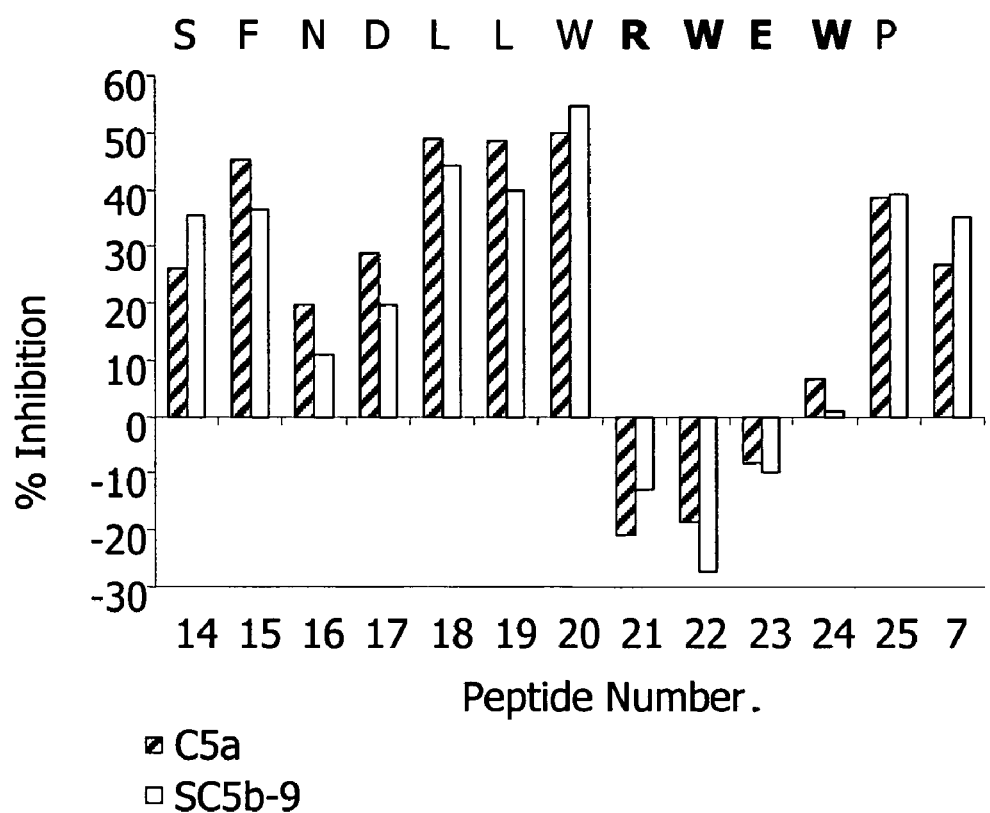
FIG. 5 is a bar graph showing percent inhibition of hemolysis for Peptides 7 and 14-25 (SEQ ID NO 7 and 14-25). Peptides 14-25 were synthesized with an alanine residue substituted at each position of the Peptide 7 sequence (shown at the top of the figure). These synthesized peptides were tested in an immune complex-classical pathway assay, measuring C5a and SC5b-9 production. See Example 7 for information regarding methodology.

Results showed that substituting an alanine for any of the residues in the consensus sequence (RWEW in Peptide 7, SEQ ID NO 7) results in loss of complement inhibiting activity (see e.g. FIG. 5). Substitution of residues L (18), L (19) or W (20), just on the amino-terminal side of the consensus sequence results in slightly greater inhibitory activity, suggesting that optimization of the residues at these positions might lead to peptides with enhanced inhibitory activity.

Example 8

Effect of Peptide Length on Inhibitory Activity

The effect of peptide length on inhibitory activity was evaluated. A series of truncated peptides were synthesized based on the structure of Peptide 13 (SEQ ID NO 13). These peptides were tested in the RBC hemolysis assay as described in Example 3 (see e.g. FIG. 6).

Figure 6:
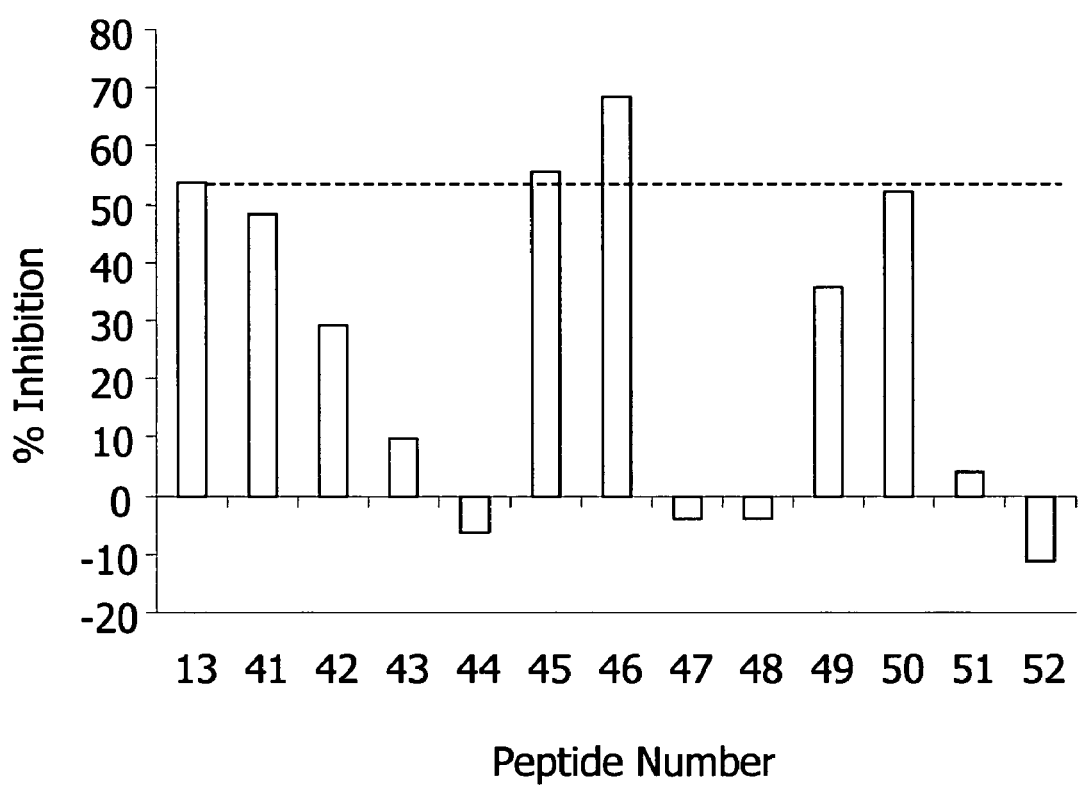
FIG. 6 is a bar graph showing percent inhibition of hemolysis for Peptides 13 and 41-52 (SEQ ID NO 13 and 41-52). Peptides 41-52 were a series of truncated peptides synthesized based on the structure of Peptide 13 (SEQ ID NO 13). These peptides were tested in the RBC hemolysis assay. See Examples 8 for information regarding methodology.

Results showed that the various peptide sequences retained at least some activity so long as at least one amino acid residue flanked the consensus sequence on the amino terminal end (see e.g. FIG. 6).

In contrast, removing the two residues from the carboxyl terminus appears to increase the activity of a peptide (peptide 46, SEQ ID NO 46), which was reduced from 12 to 10 amino acids (see e.g. FIG. 6, FIG. 10). Furthermore, removing two amino acids from both ends of a peptide (Peptide 13, SEQ ID NO 13), generates an eight-mer (Peptide 50, SEQ ID NO 50) that retains 100% of the original activity.

Figure 7:
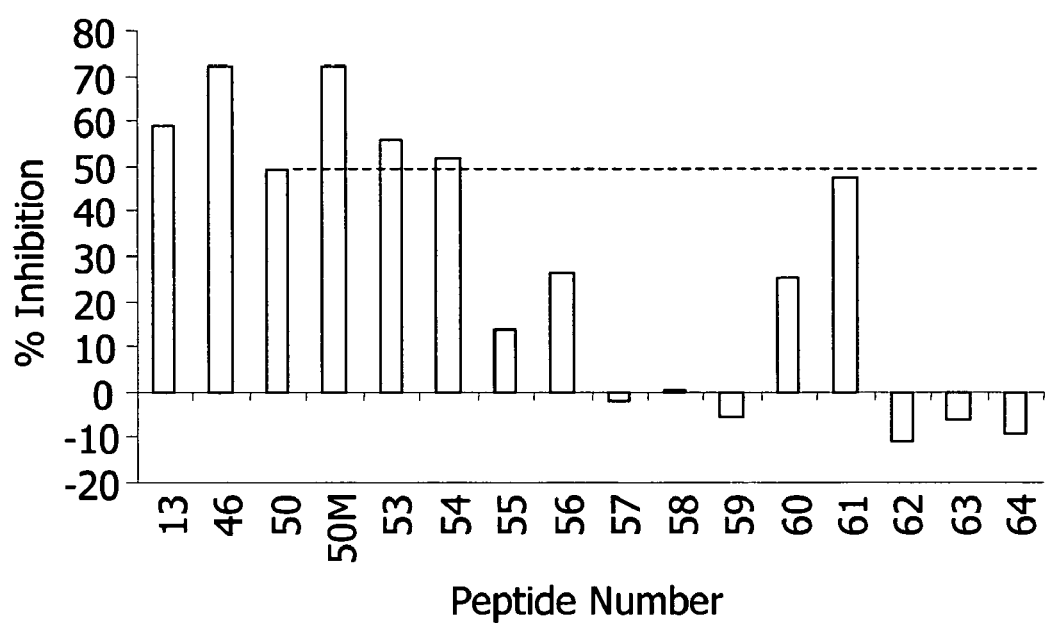
FIG. 7 is a bar graph showing percent inhibition of hemolysis for Peptides 13, 46, 50 and 53-64 (SEQ ID NO 13, 46, 50, and 53-64). Peptides 53-64 were a series of peptides made with conservative substitutions at selected sites in Peptide 50 (SEQ ID NO 50). 50M refers to a modified peptide 50 with an N-terminal acetyl and a C-terminal amide group added. All of these peptides were tested in the RBC hemolysis assay. See Example 9 for information regarding methodology.

Results also demonstrated that blocking the N-terminus (by acetylation) and the C-terminus (by amidation) of a peptide (Peptide 50, SEQ ID NO 50) increases the inhibitory activity of this peptide (see e.g. FIG. 7, FIG. 10).

Example 9

Optimization of the Consensus Sequence

The effect of substitution of similar amino acids for the consensus residues was evaluated by preparing a series of peptides making conservative substitutions at selected sites in a peptide (Peptide 50, SEQ ID NO 50). These peptides were tested in the RBC hemolysis assay as described in Example 3 (see e.g. FIG. 7).

Results showed that substitution of glutamic acid for the aspartic acid group at position 1 in Peptide 50 (SEQ ID NO 50) appeared to increase the inhibitory activity of this modified peptide (Peptide 53, SEQ ID NO 53), while substitution of asparagine for the aspartic acid residue (Peptide 54, SEQ ID NO 54) had little effect on the inhibitory activity (see e.g. FIG. 7). Changing the arginine at position 3 to either of the two other basic amino acids, lysine or histidine (Peptide 55, SEQ ID NO 55 and (Peptide 56, SEQ ID NO 56, respectively) lowers the inhibiting activity of the parent peptide. Conservative substitutions for the next two amino acids in SEQ ID NO 50 (E or W at positions 4 and 5) resulted in loss of inhibitory activity. In contrast, substituting tyrosine for the phenylalanine at position 6 (Peptide 61, SEQ ID NO 61) resulted in minimal loss of activity.

Example 10

Optimization of $X_2$

Figure 8:
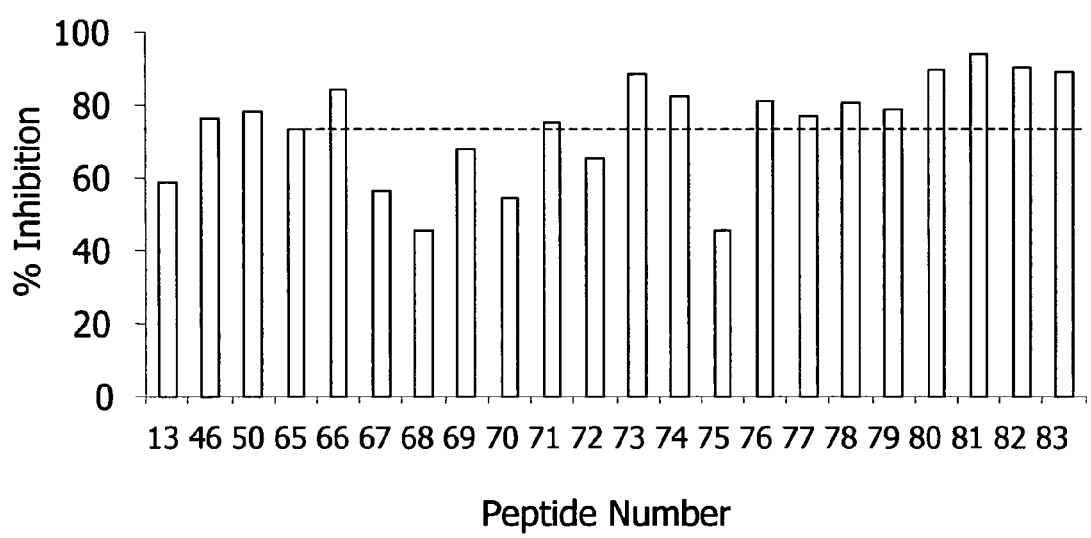
FIG. 8 is a bar graph showing percent inhibition of hemolysis for Peptides 13, 46, 50M and 65-83 (SEQ ID NO 13, 46, 50 and 65-83). Peptides 65-83 were a series of polypeptides made with randomized amino acids in the $X_2$ position of Peptide 46 (SEQ ID NO 46). 50M refers to a modified peptide 50 with an N-terminal acetyl and a C-terminal amide group added. All of these peptides were tested in the RBC hemolysis assay. See Example 10 for information regarding methodology.

Using a 10-mer peptide (Peptide 46, SEQ ID NO 46) as the basic structure (peptide 46), the $X_2$ residue was randomized (i.e. changed to every other amino acid) to generate a set of peptide derivatives. These peptides were tested in the RBC hemolysis assay as described in Example 3 (see e.g. FIG. 8). Results showed that hydrophobic side chains at this position appeared to increase the activity compared to the parent peptide.

Example 11

Optimization of $X_1$ by Substitution

Using a 10-mer peptide (Peptide 46, SEQ ID NO 46) as the basic structure, the residue a position $X_1$ was randomized (i.e. changed to every other amino acid) to generate a set of peptide derivatives. These peptides were tested in the RBC hemolysis assay as described in Example 3 (see e.g. FIG. 9).

Figure 9:
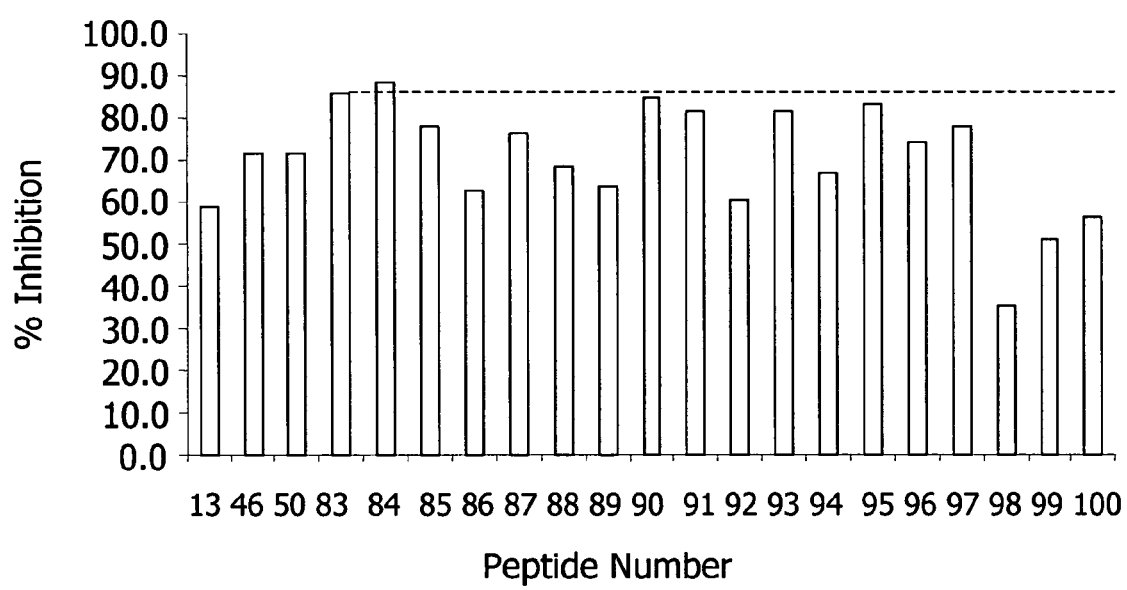
FIG. 9. is a bar graph showing percent inhibition of hemolysis for Peptides 13, 46, 50 M and 83-100 (SEQ ID NO 13, 46, 50 and 83-100). Peptides 84-100 were a series of polypeptides made with randomized amino acids in the $X_1$ position of Peptide 46. 50M refers to a modified peptide 50 with an N-terminal acetyl and a C-terminal amide group added. All of these peptides were tested in the RBC hemolysis assay. See Example 11 for information regarding methodology.

Results showed that two peptides (Peptide 83, SEQ ID NO 83 and (Peptide 84, SEQ ID NO 84) with a glutamic acid at $X_1$ had the highest level of inhibitory activity (see e.g. FIG. 9, FIG. 10). Substitutions with almost comparable activity included aspartic acid (Peptide 13, SEQ ID NO 13), isoleucine (Peptide 90, SEQ ID NO 90), leucine (Peptide 91, SEQ ID NO 91), and proline (Peptide 95, SEQ ID NO 95).

Example 12

Reduction and Alkylation of Cysteine

In exploring the role of the cysteine residues of the cyclized polypeptide (see e.g. Peptide 6, SEQ ID NO 6), both cysteines were reduced and alkylated, and the resulting polypeptides were tested via hemolysis assay (see e.g. Example 3). Reduction and alkylation of sulfhydryl groups is well known in the art (see e.g. Crestfield et al. (1963) J. Biol. Chem. 238:622-627).

Reduction and alkylation of the disulfide bond in the peptide was carried out by incubation peptide with a 10 fold molar excess of DTT in degassed 250 mM Tris pH 8.5 for 2 hours. The reaction was quenched by the addition of a 50 fold molar excess of iodoacetamide and allowed to react for an additional hour. The reduced and alkylated peptide was purified over an RP-8 column on a Waters 490 HPLC with a gradient of acetonitrile from 0-80%, containing 0.1% trifluoroacetic acid.

Results showed that complement-related activity of Peptide 6 was lost when the sulfhydryl groups of the cysteine amino acid residues in SEQ ID NO 6 were reduced or alkylated. This indicates that the disulfide linkage is necessary for the function of Peptide 6.

Example 13

Alanine Scanning of the Z Peptide

Figure 11:
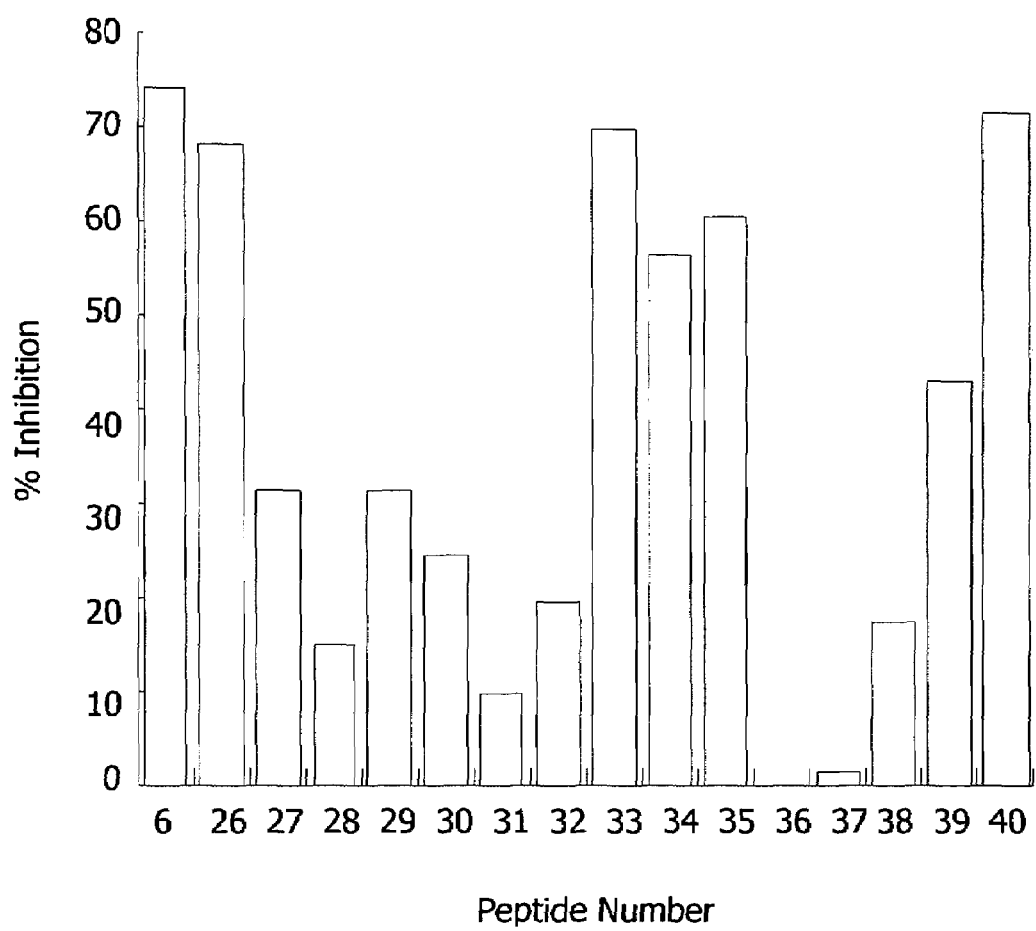
FIG. 11 is a bar graph showing percent inhibition of hemolysis for Peptides 6 and 26-40 (SEQ ID NO 6 and 26-40). Peptides 26-40 were peptides either synthesized with an alanine residue substituted at each position of the Peptide 6 sequence or truncated peptides based upon the peptide 6 sequence. These synthesized peptides were tested in a hemolysis assay. See Example 13 and 14 for information regarding methodology.

Alanine scanning was used to discern particular residues in the cyclized polypeptide, aside from the cysteine amino acid residues, that contributed to its activity. This method, well known in the art (Morison and Weiss (2001), Current Opinions in Chemical Biology 5:302-307; Cunningham and Wells (1989), Science 244:1081-1085), involved substituting an alanine residue at each position in a sequence and testing the resulting peptide derivative for activity (see e.g. Example 7). Loss of activity suggested that particular residue in the parent peptide plays a role in the function of the molecule. Various peptides were synthesized with an alanine residue substituted at each position of the sequence of Peptide 6 (SEQ ID NO 6). These peptides were tested in a classical hemolysis assay (see e.g. Example 3). Results showed that substitution of alanine residues for either the proline or tryptophan amino acid residues of Peptide 6 resulted in the loss of activity (see e.g. FIG. 11).

Example 14

Truncation of the Z Peptide

To evaluate the effect of peptide length on inhibitory activity of cyclized polypeptides, a series of truncated peptides were synthesized based on the structure of Peptide 6 (SEQ ID NO 6). Truncation methodology is well known in the art (Fields (1997), Methods in Enzymology 289). Results showed that polypeptides with cysteine residues on both the amino- and carboxy-terminus retained activity (see e.g. FIG. 11). Results also indicated that activity of the cyclized peptide was enhanced as more amino acid residues were added to the ends.

Example 15

Optimization of $X_1$ by Extension of the Peptide

Using a 10-mer peptide (SEQ ID NO 46) as the basic structure, tri-peptides were substituted for $X_1$, where either the first or second amino acid of the tri-peptides were changed to amino acids with different functional groups (i.e. acidic, basic, hydrophobic, polar, and aromatic) and the third amino acid was a glutamic acid. These peptides (SEQ ID NOs 112-121) were tested in the RBC hemolysis assay as described in Example 3 (see e.g. FIG. 12).

Figure 12:
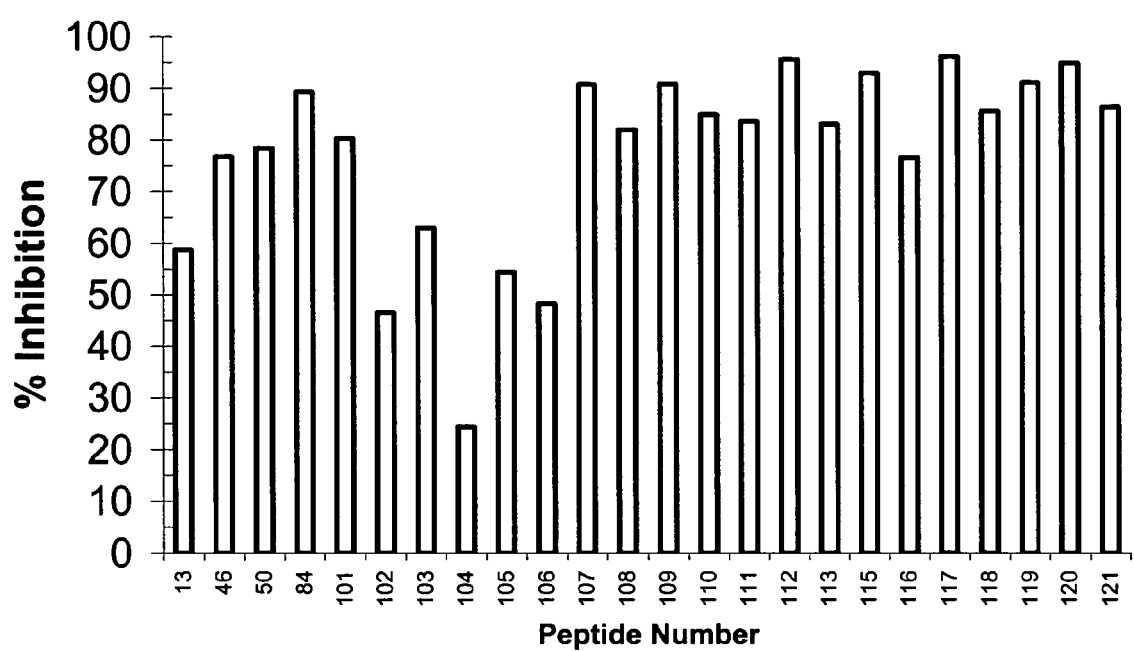
FIG. 12 is a bar graph showing percent inhibition of hemolysis for Peptides 13, 46, 50, 84, and 101-121. Peptides 101-121 were a series of polypeptides made with amino acids of different functional groups substituted in the $X_1$ position (Peptides 112-121), the $X_5$ position (Peptides 101-106), and the $X_6$ position (Peptides 107-111). All of these peptides were tested in the RBC hemolyis assay. See examples 15-17 for information regarding methodology.

Results showed that six peptides (SEQ ID NOs 84, 112, 115, 117, 119, and 120) with acidic (glutamic acid), polar (threonine), or hydrophobic (leucine) amino acids at either the first or second positions of the tri-peptide enhanced the levels of inhibitory activity (see e.g. FIG. 10, FIG. 12). All of the other substitutions were of almost comparable activity.

Example 16

Optimization of $X_5$

Using a 10-mer peptide (SEQ ID NO 46) as the basic structure, substitutions were made at the $X_5$ position to amino acids with different functional groups (i.e. acidic, basic, hydrophobic, polar, and aromatic) to generate a set of derivatives. These peptides (SEQ ID NOs 101-106) were tested in the RBC hemolysis assay as described in Example 3 (see e.g. FIG. 12).

Results showed that the original amino acid of proline, which allows unique structural conformations, had the highest level of inhibitory activity, while none of the substitutions abolished activity (see e.g. FIG. 12).

Example 17

Optimization of $X_6$

Using a 10-mer peptide (SEQ ID NO 46) as the basic structure, substitutions were made at the $X_6$ position to amino acids with different functional groups (i.e. acidic, basic, hydrophobic, polar, and aromatic) to generate a set of derivatives. These peptides (SEQ ID NOs 107-111) were tested in the RBC hemolysis assay as described in Example 3 (see e.g. FIG. 12).

Results showed that substitution with an acidic (glutamic acid) or polar (glutamine) amino acid at this position results in slightly elevated inhibitory activity (see e.g. FIG. 12). However all substitutions at this residue gave relatively comparable inhibitory activity.

Example 18

Inhibition of Cell Death

The peptides were evaluated for their ability to inhibit complement mediated cell death in an in vitro autoimmune glomerulonephritis model. Human mesangial cells were cultured to approximately 75% confluency and then treated for one hour at 37° C. with phosphatidyl inositol-phospholipase C to remove GPI-anchored complement regulatory proteins. Following enzyme treatment, the cells were washed and equilibrated in GSBM growth medium supplemented with 2.5% fetal bovine serum for one hour at 37° C. The cells were then incubated in pooled human plasma supplemented with 100 µg/mL of heat aggregated human IVIG (generated by heating at 63° C. for 30 minutes) either in the presence of absence of various concentrations of peptides for 48 hours at 37° C. The source of complement was replenished every 12 hours during the incubation by adding 25% of the original volume of fresh plasma along with heat aggregated IVIG and peptides so that the same final concentrations were maintained. Following the 48 hour incubation, the cells were stained with the commercial Live/Dead Viability kit (Molecular Probes) and the relative fluorescence was measured to determine the extent of cell death. The percent of cell death was calculated versus a control sample in which heat-inactivated plasma, (heated to 56° C. for 30 minutes) as a means of inactivating complement components, was used.

Figure 13:
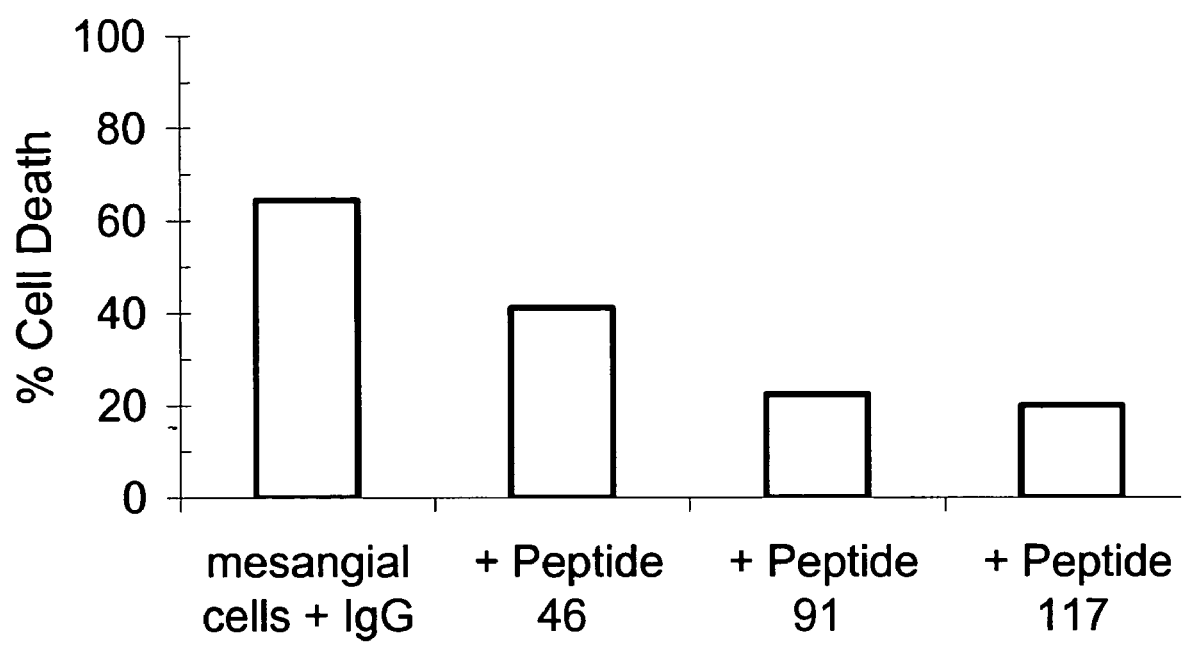
FIG. 13 is a bar graph showing the extent of human mesangial cell death after exposure to immune complexes in the presence and absence of peptides 46, 91, and 117. See Example 18 for information regarding methodology.
Figure 14:
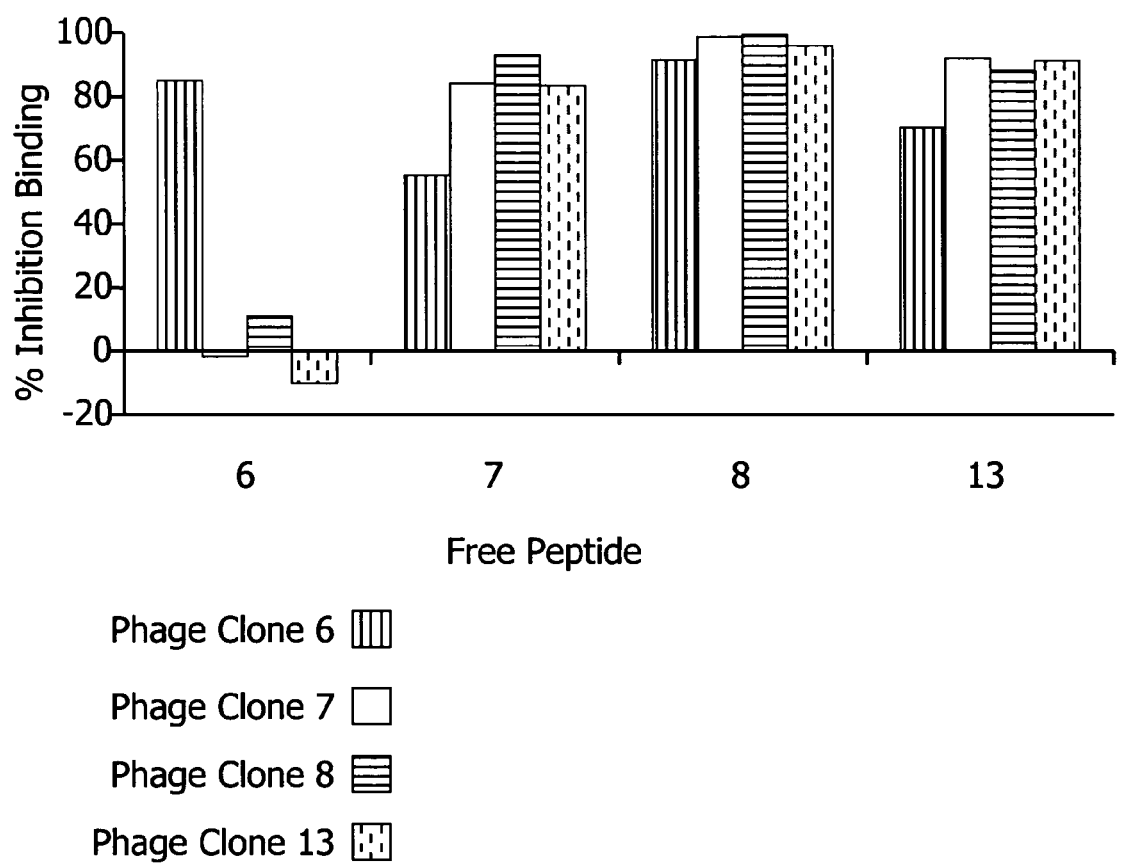
FIG. 14 is a bar graph showing the competition of free peptides 6, 7, 8, and 13 with phage clones 6, 7, 8, and 13 for binding to C5. Plotted is the percentage that 50 μM concentration of each free peptide inhibits the phage clone from binding to C5. See Example 2 for information regarding methodology.

Results showed that at concentrations of 250 µM of peptide, optimized peptides (SEQ ID NO 117) could inhibit complement mediated cell death by up to 69% (see e.g. FIG. 13). The relative levels of inhibition of cell death obtained by the three peptides shown (SEQ ID NOs 46, 91, and 117) follow the same trend as the relative levels of inhibition seen for these three peptides in the RBC hemolysis assays (see e.g. FIG. 9, FIG. 12, FIG. 13).

What is claimed is:

1. A composition comprising a polypeptide consisting of a sequence $X_1$-$X_2$-$X_3$-W-E-$X_4$-$X_5$-$X_6$, wherein:
   E is a glutamic acid residue;
   W is a tryptophan residue;
   $X_1$ is a sequence of one to five amino acid residues;
   $X_2$ is an amino acid residue selected from the group consisting of asparagine, alanine, glutamic acid, glycine, histidine, isoleucine, leucine, methionine, phenylalanine, proline, tryptophan, tyrosine and valine;
   $X_3$ is arginine;
   $X_4$ is phenylalanine or tyrosine;
   $X_5$ is proline; and
   $X_6$ is a sequence of one to five amino acid residues wherein the polypeptide has a total number of amino acid residues ranging from 8 to about 15.

2. The composition of claim 1 wherein $X_1$ is a glutamic acid residue.

3. The composition of claim 1 wherein $X_6$ is an amino acid residue.

4. The composition of claim 3 wherein $X_6$ is an acidic amino acid residue or a polar amino acid residue.

5. The composition of claim 4 wherein $X_6$ is a glutamic acid residue or a glutamine residue.

6. The composition of claim 1 wherein $X_2$ is selected from the group consisting of tryptophan, tyrosine, valine, threonine, isoleucine, alanine, glutamic acid, and leucine.

7. The composition of claim 6 wherein $X_2$ is selected from the group consisting of valine, threonine, and leucine.

8. The composition of claim 7 wherein $X_2$ is a valine residue.

9. The composition of claim 1 wherein $X_4$ is a phenylalanine residue.

10. The composition of claim 1 wherein $X_5$ is a proline residue.

11. The composition of claim 1 wherein the polypeptide has an amino-terminal acetyl group.

12. The composition of claim 1 wherein the polypeptide has a carboxy-terminal amide group.

13. The composition of claim 1 wherein the composition further comprises a pharmaceutically acceptable carrier, excipient, stabilizer, or diluent.

14. The composition of claim 1 wherein one or more of the following conditions are satisfied:

$X_1$ is a glutamic acid residue;
$X_2$ is a valine residue;
$X_4$ is a phenylalanine residue;
$X_6$ is a glutamic acid residue;
the polypeptide has an amino-terminal acetyl group;
the polypeptide has a carboxy-terminal amide group; or
the composition further comprises a pharmaceutically acceptable carrier, excipient, stabilizer, or diluent.

15. A composition comprising a polypeptide comprising a sequence selected from the group consisting of SEQ ID NO 7, SEQ ID NO 8, SEQ ID NO 13, SEQ ID NO 46, SEQ ID NO 50, SEQ ID NO 65, SEQ ID NO 66, SEQ ID NO 69, SEQ ID NO 73, SEQ ID NO 74, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 103, SEQ ID NO 107, SEQ ID NO 108, SEQ ID NO 109, SEQ ID NO 110, SEQ ID NO 111, SEQ ID NO 112, SEQ ID NO 113, SEQ ID NO 114, SEQ ID NO 115, SEQ ID NO 116, SEQ ID NO 117, SEQ ID NO 118, SEQ ID NO 119, SEQ ID NO 120, and SEQ ID NO 121.

16. The composition of claim 15 wherein the polypeptide comprises a sequence selected from the group consisting of SEQ ID NO 46, SEQ ID NO 50, SEQ ID NO 66, SEQ ID NO 73, SEQ ID NO 74, SEQ ID NO 76, SEQ ID NO 78, SEQ ID NO 80, SEQ ID NO 81, SEQ ID NO 82, SEQ ID NO 83, SEQ ID NO 84, SEQ ID NO 90, SEQ ID NO 91, SEQ ID NO 93, SEQ ID NO 95, SEQ ID NO 107, SEQ ID NO 109, SEQ ID NO 112, SEQ ID NO 113, SEQ ID NO 115, SEQ ID NO 117, SEQ ID NO 119, and SEQ ID NO 120.

17. The composition of claim 16 wherein the polypeptide comprises a sequence selected from the group consisting of SEQ ID NO 73, SEQ ID NO 80, SEQ ID NO 81, SEQ ID NO 82, SEQ ID NO 83, SEQ ID NO 84, SEQ ID NO 90, SEQ ID NO 91, SEQ ID NO 93, SEQ ID NO 95, SEQ ID NO 107, SEQ ID NO 109, SEQ ID NO 112, SEQ ID NO 115, SEQ ID NO 117, SEQ ID NO 119, and SEQ ID NO 120.

18. The composition of claim 17 wherein the polypeptide comprises a sequence selected from the group consisting of SEQ ID NO 112, 115, 117, and 120.

19. The composition of claim 18 wherein the polypeptide comprises SEQ ID NO 112.

20. The composition of claim 15 wherein the composition further comprises a pharmaceutically acceptable carrier, excipient, stabilizer, or diluent.

21. A method of inhibiting complement activation comprising applying the composition of claim 1 to a surface of a medical device, or a surface of an organ before transplantation.

22. The method of claim 21 wherein the medical device is a stent.

* * * * *

```
                        SEQUENCE LISTING

<160> NUMBER OF SEQ ID NOS: 121

<210> SEQ ID NO 1
<211> LENGTH: 12
<212> TYPE: PRT
<213> ORGANISM: Artificial Sequence
<220> FEATURE:
<223> OTHER INFORMATION: complement inhibitor

<400> SEQUENCE: 1

Lys Leu Asp His Arg Asn Pro Ser Gly Trp Asp Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: complement inhibitor

<400> SEQUENCE: 2

Asn Met Gln Ser Arg Met Leu His Gln Ile Leu Asp
1               5                   10

<210> SEQ ID NO 3
<211> LENGTH: 12
<212> TYPE: PRT
<213> ORGANISM: Artificial Sequence
<220> FEATURE:
<223> OTHER INFORMATION: complement inhibitor

<400> SEQUENCE: 3

Ser Tyr Pro Gln His His Gln Ala Ala Thr Tyr Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: complement inhibitor

<400> SEQUENCE: 4

Met Asn Ala Val Gln Ser Pro Phe Ala Thr Pro Leu
```

```
<210> SEQ ID NO 5
<211> LENGTH: 12
<212> TYPE: PRT
<213> ORGANISM: Artificial Sequence
<220> FEATURE:
<223> OTHER INFORMATION: complement inhibitor

<400> SEQUENCE: 5

Trp Lys Ala Pro Tyr Phe Thr Leu Gln Thr Leu Asp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: complement inhibitor

<400> SEQUENCE: 6

Ser Asp Met Cys Ala Ala Pro Trp Leu Cys Pro Val
1               5                   10

<210> SEQ ID NO 7
<211> LENGTH: 12
<212> TYPE: PRT
<213> ORGANISM: Artificial Sequence
<220> FEATURE:
<223> OTHER INFORMATION: complement inhibitor

<400> SEQUENCE: 7

Ser Phe Asn Asp Leu Leu Trp Arg Trp Glu Trp Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: complement inhibitor

<400> SEQUENCE: 8

Asp Ser Thr Trp Thr Asn Phe Arg Trp Glu Phe Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: complement inhibitor

<400> SEQUENCE: 9

Ser Lys Pro Leu Ser His Gly Pro Tyr Phe Thr Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: complement inhibitor

<400> SEQUENCE: 10

Phe Ser Leu His Met Pro Pro Val Pro Val Pro Ala
1               5                   10
```

```
<210> SEQ ID NO 11
<211> LENGTH: 12
<212> TYPE: PRT
<213> ORGANISM: Artificial Sequence
<220> FEATURE:
<223> OTHER INFORMATION: complement inhibitor

<400> SEQUENCE: 11

Thr Leu Thr Pro Tyr Ser Ala Ser Val Ser Pro Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: complement inhibitor

<400> SEQUENCE: 12

Gly Cys Ser Thr Glu His Ser Cys Ser Asn Gln His
1               5                   10

<210> SEQ ID NO 13
<211> LENGTH: 12
<212> TYPE: PRT
<213> ORGANISM: Artificial Sequence
<220> FEATURE:
<223> OTHER INFORMATION: complement inhibitor

<400> SEQUENCE: 13

Thr Gln Asp Asn Arg Trp Glu Phe Pro Leu Arg Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: complement inhibitor

<400> SEQUENCE: 14

Ala Phe Asn Asp Leu Leu Trp Arg Trp Glu Trp Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: complement inhibitor

<400> SEQUENCE: 15

Ser Ala Asn Asp Leu Leu Trp Arg Trp Glu Trp Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: complement inhibitor

<400> SEQUENCE: 16

Ser Phe Ala Asp Leu Leu Trp Arg Trp Glu Trp Pro
1               5                   10
```

```
<210> SEQ ID NO 17
<211> LENGTH: 12
<212> TYPE: PRT
<213> ORGANISM: Artificial Sequence
<220> FEATURE:
<223> OTHER INFORMATION: complement inhibitor

<400> SEQUENCE: 17

Ser Phe Asn Ala Leu Leu Trp Arg Trp Glu Trp Pro
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: complement inhibitor

<400> SEQUENCE: 18

Ser Phe Asn Asp Ala Leu Trp Arg Trp Glu Trp Pro
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: complement inhibitor

<400> SEQUENCE: 19

Ser Phe Asn Asp Leu Ala Trp Arg Trp Glu Trp Pro
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: complement inhibitor

<400> SEQUENCE: 20

Ser Phe Asn Asp Leu Leu Ala Arg Trp Glu Trp Pro
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: complement inhibitor

<400> SEQUENCE: 21

Ser Phe Asn Asp Leu Leu Trp Ala Trp Glu Trp Pro
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: complement inhibitor

<400> SEQUENCE: 22

Ser Phe Asn Asp Leu Leu Trp Arg Ala Glu Trp Pro
 1               5                  10
```

```
<210> SEQ ID NO 23
<211> LENGTH: 12
<212> TYPE: PRT
<213> ORGANISM: Artificial Sequence
<220> FEATURE:
<223> OTHER INFORMATION: complement inhibitor

<400> SEQUENCE: 23

Ser Phe Asn Asp Leu Leu Trp Arg Trp Ala Trp Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: complement inhibitor

<400> SEQUENCE: 24

Ser Phe Asn Asp Leu Leu Trp Arg Trp Glu Ala Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: complement inhibitor

<400> SEQUENCE: 25

Ser Phe Asn Asp Leu Leu Trp Arg Trp Glu Trp Ala
1               5                   10

<210> SEQ ID NO 26
<211> LENGTH: 11
<212> TYPE: PRT
<213> ORGANISM: Artificial Sequence
<220> FEATURE:
<223> OTHER INFORMATION: complement inhibitor

<400> SEQUENCE: 26

Asp Met Cys Ala Ala Pro Trp Leu Cys Pro Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: complement inhibitor

<400> SEQUENCE: 27

Met Cys Ala Ala Pro Trp Leu Cys Pro Val
1               5                   10

<210> SEQ ID NO 28
<211> LENGTH: 9
<212> TYPE: PRT
<213> ORGANISM: Artificial Sequence
<220> FEATURE:
<223> OTHER INFORMATION: complement inhibitor

<400> SEQUENCE: 28

Cys Ala Ala Pro Trp Leu Cys Pro Val
1               5

<210> SEQ ID NO 29
```

```
<211> LENGTH: 11
<212> TYPE: PRT
<213> ORGANISM: Artificial Sequence
<220> FEATURE:
<223> OTHER INFORMATION: complement inhibitor

<400> SEQUENCE: 29

Ser Asp Met Cys Ala Ala Pro Trp Leu Cys Pro
1               5                   10

<210> SEQ ID NO 30
<211> LENGTH: 10
<212> TYPE: PRT
<213> ORGANISM: Artificial Sequence
<220> FEATURE:
<223> OTHER INFORMATION: complement inhibitor

<400> SEQUENCE: 30

Ser Asp Met Cys Ala Ala Pro Trp Leu Cys
1               5                   10

<210> SEQ ID NO 31
<211> LENGTH: 8
<212> TYPE: PRT
<213> ORGANISM: Artificial Sequence
<220> FEATURE:
<223> OTHER INFORMATION: complement inhibitor

<400> SEQUENCE: 31

Cys Ala Ala Pro Trp Leu Cys Pro
1               5

<210> SEQ ID NO 32
<211> LENGTH: 7
<212> TYPE: PRT
<213> ORGANISM: Artificial Sequence
<220> FEATURE:
<223> OTHER INFORMATION: complement inhibitor

<400> SEQUENCE: 32

Cys Ala Ala Pro Trp Leu Cys
1               5

<210> SEQ ID NO 33
<211> LENGTH: 12
<212> TYPE: PRT
<213> ORGANISM: Artificial Sequence
<220> FEATURE:
<223> OTHER INFORMATION: complement inhibitor

<400> SEQUENCE: 33

Ala Asp Met Cys Ala Ala Pro Trp Leu Cys Pro Val
1               5                   10

<210> SEQ ID NO 34
<211> LENGTH: 12
<212> TYPE: PRT
<213> ORGANISM: Artificial Sequence
<220> FEATURE:
<223> OTHER INFORMATION: complement inhibitor

<400> SEQUENCE: 34

Ser Ala Met Cys Ala Ala Pro Trp Leu Cys Pro Val
1               5                   10

<210> SEQ ID NO 35
<211> LENGTH: 12
```

<212> TYPE: PRT
<213> ORGANISM: Artificial Sequence
<220> FEATURE:
<223> OTHER INFORMATION: complement inhibitor

<400> SEQUENCE: 35

Ser Asp Ala Cys Ala Ala Pro Trp Leu Cys Pro Val
1               5                   10

<210> SEQ ID NO 36
<211> LENGTH: 12
<212> TYPE: PRT
<213> ORGANISM: Artificial Sequence
<220> FEATURE:
<223> OTHER INFORMATION: complement inhibitor

<400> SEQUENCE: 36

Ser Asp Met Cys Ala Ala Ala Trp Leu Cys Pro Val
1               5                   10

<210> SEQ ID NO 37
<211> LENGTH: 12
<212> TYPE: PRT
<213> ORGANISM: Artificial Sequence
<220> FEATURE:
<223> OTHER INFORMATION: complement inhibitor

<400> SEQUENCE: 37

Ser Asp Met Cys Ala Ala Pro Ala Leu Cys Pro Val
1               5                   10

<210> SEQ ID NO 38
<211> LENGTH: 12
<212> TYPE: PRT
<213> ORGANISM: Artificial Sequence
<220> FEATURE:
<223> OTHER INFORMATION: complement inhibitor

<400> SEQUENCE: 38

Ser Asp Met Cys Ala Ala Pro Trp Ala Cys Pro Val
1               5                   10

<210> SEQ ID NO 39
<211> LENGTH: 12
<212> TYPE: PRT
<213> ORGANISM: Artificial Sequence
<220> FEATURE:
<223> OTHER INFORMATION: complement inhibitor

<400> SEQUENCE: 39

Ser Asp Met Cys Ala Ala Pro Trp Leu Cys Ala Val
1               5                   10

<210> SEQ ID NO 40
<211> LENGTH: 12
<212> TYPE: PRT
<213> ORGANISM: Artificial Sequence
<220> FEATURE:
<223> OTHER INFORMATION: complement inhibitor

<400> SEQUENCE: 40

Ser Asp Met Cys Ala Ala Pro Trp Leu Cys Pro Ala
1               5                   10

<210> SEQ ID NO 41
<211> LENGTH: 11
<212> TYPE: PRT

```
<213> ORGANISM: Artificial Sequence
<220> FEATURE:
<223> OTHER INFORMATION: complement inhibitor

<400> SEQUENCE: 41

Gln Asp Asn Arg Trp Glu Phe Pro Leu Arg Val
1               5                   10

<210> SEQ ID NO 42
<211> LENGTH: 10
<212> TYPE: PRT
<213> ORGANISM: Artificial Sequence
<220> FEATURE:
<223> OTHER INFORMATION: complement inhibitor

<400> SEQUENCE: 42

Asp Asn Arg Trp Glu Phe Pro Leu Arg Val
1               5                   10

<210> SEQ ID NO 43
<211> LENGTH: 9
<212> TYPE: PRT
<213> ORGANISM: Artificial Sequence
<220> FEATURE:
<223> OTHER INFORMATION: complement inhibitor

<400> SEQUENCE: 43

Asn Arg Trp Glu Phe Pro Leu Arg Val
1               5

<210> SEQ ID NO 44
<211> LENGTH: 8
<212> TYPE: PRT
<213> ORGANISM: Artificial Sequence
<220> FEATURE:
<223> OTHER INFORMATION: complement inhibitor

<400> SEQUENCE: 44

Arg Trp Glu Phe Pro Leu Arg Val
1               5

<210> SEQ ID NO 45
<211> LENGTH: 11
<212> TYPE: PRT
<213> ORGANISM: Artificial Sequence
<220> FEATURE:
<223> OTHER INFORMATION: complement inhibitor

<400> SEQUENCE: 45

Thr Gln Asp Asn Arg Trp Glu Phe Pro Leu Arg
1               5                   10

<210> SEQ ID NO 46
<211> LENGTH: 10
<212> TYPE: PRT
<213> ORGANISM: Artificial Sequence
<220> FEATURE:
<223> OTHER INFORMATION: complement inhibitor

<400> SEQUENCE: 46

Thr Gln Asp Asn Arg Trp Glu Phe Pro Leu
1               5                   10

<210> SEQ ID NO 47
<211> LENGTH: 9
<212> TYPE: PRT
<213> ORGANISM: Artificial Sequence
```

```
<220> FEATURE:
<223> OTHER INFORMATION: complement inhibitor

<400> SEQUENCE: 47

Thr Gln Asp Asn Arg Trp Glu Phe Pro
1               5

<210> SEQ ID NO 48
<211> LENGTH: 8
<212> TYPE: PRT
<213> ORGANISM: Artificial Sequence
<220> FEATURE:
<223> OTHER INFORMATION: complement inhibitor

<400> SEQUENCE: 48

Thr Gln Asp Asn Arg Trp Glu Phe
1               5

<210> SEQ ID NO 49
<211> LENGTH: 10
<212> TYPE: PRT
<213> ORGANISM: Artificial Sequence
<220> FEATURE:
<223> OTHER INFORMATION: complement inhibitor

<400> SEQUENCE: 49

Gln Asp Asn Arg Trp Glu Phe Pro Leu Arg
1               5                   10

<210> SEQ ID NO 50
<211> LENGTH: 8
<212> TYPE: PRT
<213> ORGANISM: Artificial Sequence
<220> FEATURE:
<223> OTHER INFORMATION: complement inhibitor

<400> SEQUENCE: 50

Asp Asn Arg Trp Glu Phe Pro Leu
1               5

<210> SEQ ID NO 51
<211> LENGTH: 6
<212> TYPE: PRT
<213> ORGANISM: Artificial Sequence
<220> FEATURE:
<223> OTHER INFORMATION: complement inhibitor

<400> SEQUENCE: 51

Asn Arg Trp Glu Phe Pro
1               5

<210> SEQ ID NO 52
<211> LENGTH: 4
<212> TYPE: PRT
<213> ORGANISM: Artificial Sequence
<220> FEATURE:
<223> OTHER INFORMATION: complement inhibitor

<400> SEQUENCE: 52

Arg Trp Glu Phe
1

<210> SEQ ID NO 53
<211> LENGTH: 8
<212> TYPE: PRT
<213> ORGANISM: Artificial Sequence
<220> FEATURE:
```

<223> OTHER INFORMATION: complement inhibitor

<400> SEQUENCE: 53

Glu Asn Arg Trp Glu Phe Pro Leu
1               5

<210> SEQ ID NO 54
<211> LENGTH: 8
<212> TYPE: PRT
<213> ORGANISM: Artificial Sequence
<220> FEATURE:
<223> OTHER INFORMATION: complement inhibitor

<400> SEQUENCE: 54

Asn Asn Arg Trp Glu Phe Pro Leu
1               5

<210> SEQ ID NO 55
<211> LENGTH: 8
<212> TYPE: PRT
<213> ORGANISM: Artificial Sequence
<220> FEATURE:
<223> OTHER INFORMATION: complement inhibitor

<400> SEQUENCE: 55

Asp Asn Lys Trp Glu Phe Pro Leu
1               5

<210> SEQ ID NO 56
<211> LENGTH: 8
<212> TYPE: PRT
<213> ORGANISM: Artificial Sequence
<220> FEATURE:
<223> OTHER INFORMATION: complement inhibitor

<400> SEQUENCE: 56

Asp Asn His Trp Glu Phe Pro Leu
1               5

<210> SEQ ID NO 57
<211> LENGTH: 8
<212> TYPE: PRT
<213> ORGANISM: Artificial Sequence
<220> FEATURE:
<223> OTHER INFORMATION: complement inhibitor

<400> SEQUENCE: 57

Asp Asn Arg Phe Glu Phe Pro Leu
1               5

<210> SEQ ID NO 58
<211> LENGTH: 8
<212> TYPE: PRT
<213> ORGANISM: Artificial Sequence
<220> FEATURE:
<223> OTHER INFORMATION: complement inhibitor

<400> SEQUENCE: 58

Asp Asn Arg Tyr Glu Phe Pro Leu
1               5

<210> SEQ ID NO 59
<211> LENGTH: 8
<212> TYPE: PRT
<213> ORGANISM: Artificial Sequence
<220> FEATURE:
<223> OTHER INFORMATION: complement inhibitor

```
<400> SEQUENCE: 59

Asp Asn Arg Trp Asp Phe Pro Leu
1               5

<210> SEQ ID NO 60
<211> LENGTH: 8
<212> TYPE: PRT
<213> ORGANISM: Artificial Sequence
<220> FEATURE:
<223> OTHER INFORMATION: complement inhibitor

<400> SEQUENCE: 60

Asp Asn Arg Trp Glu Trp Pro Leu
1               5

<210> SEQ ID NO 61
<211> LENGTH: 8
<212> TYPE: PRT
<213> ORGANISM: Artificial Sequence
<220> FEATURE:
<223> OTHER INFORMATION: complement inhibitor

<400> SEQUENCE: 61

Asp Asn Arg Trp Glu Tyr Pro Leu
1               5

<210> SEQ ID NO 62
<211> LENGTH: 8
<212> TYPE: PRT
<213> ORGANISM: Artificial Sequence
<220> FEATURE:
<223> OTHER INFORMATION: complement inhibitor

<400> SEQUENCE: 62

Asp Asn Arg Leu Glu Phe Pro Leu
1               5

<210> SEQ ID NO 63
<211> LENGTH: 8
<212> TYPE: PRT
<213> ORGANISM: Artificial Sequence
<220> FEATURE:
<223> OTHER INFORMATION: complement inhibitor

<400> SEQUENCE: 63

Asp Asn Arg Trp Gln Phe Pro Leu
1               5

<210> SEQ ID NO 64
<211> LENGTH: 8
<212> TYPE: PRT
<213> ORGANISM: Artificial Sequence
<220> FEATURE:
<223> OTHER INFORMATION: complement inhibitor

<400> SEQUENCE: 64

Asp Asn Arg Trp Glu Leu Pro Leu
1               5

<210> SEQ ID NO 65
<211> LENGTH: 10
<212> TYPE: PRT
<213> ORGANISM: Artificial Sequence
<220> FEATURE:
<223> OTHER INFORMATION: complement inhibitor
```

-continued

<400> SEQUENCE: 65

Ala Ala Glu Asn Arg Trp Glu Phe Pro Leu
1               5                   10

<210> SEQ ID NO 66
<211> LENGTH: 10
<212> TYPE: PRT
<213> ORGANISM: Artificial Sequence
<220> FEATURE:
<223> OTHER INFORMATION: complement inhibitor

<400> SEQUENCE: 66

Ala Ala Glu Ala Arg Trp Glu Phe Pro Leu
1               5                   10

<210> SEQ ID NO 67
<211> LENGTH: 10
<212> TYPE: PRT
<213> ORGANISM: Artificial Sequence
<220> FEATURE:
<223> OTHER INFORMATION: complement inhibitor

<400> SEQUENCE: 67

Ala Ala Glu Arg Arg Trp Glu Phe Pro Leu
1               5                   10

<210> SEQ ID NO 68
<211> LENGTH: 10
<212> TYPE: PRT
<213> ORGANISM: Artificial Sequence
<220> FEATURE:
<223> OTHER INFORMATION: complement inhibitor

<400> SEQUENCE: 68

Ala Ala Glu Asp Arg Trp Glu Phe Pro Leu
1               5                   10

<210> SEQ ID NO 69
<211> LENGTH: 10
<212> TYPE: PRT
<213> ORGANISM: Artificial Sequence
<220> FEATURE:
<223> OTHER INFORMATION: complement inhibitor

<400> SEQUENCE: 69

Ala Ala Glu Glu Arg Trp Glu Phe Pro Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: complement inhibitor

<400> SEQUENCE: 70

Ala Ala Glu Gln Arg Trp Glu Phe Pro Leu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: complement inhibitor

<400> SEQUENCE: 71

```
Ala Ala Glu Gly Arg Trp Glu Phe Pro Leu
1               5                   10

<210> SEQ ID NO 72
<211> LENGTH: 10
<212> TYPE: PRT
<213> ORGANISM: Artificial Sequence
<220> FEATURE:
<223> OTHER INFORMATION: complement inhibitor

<400> SEQUENCE: 72

Ala Ala Glu His Arg Trp Glu Phe Pro Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: complement inhibitor

<400> SEQUENCE: 73

Ala Ala Glu Ile Arg Trp Glu Phe Pro Leu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: complement inhibitor

<400> SEQUENCE: 74

Ala Ala Glu Leu Arg Trp Glu Phe Pro Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: complement inhibitor

<400> SEQUENCE: 75

Ala Ala Glu Lys Arg Trp Glu Phe Pro Leu
1               5                   10

<210> SEQ ID NO 76
<211> LENGTH: 10
<212> TYPE: PRT
<213> ORGANISM: Artificial Sequence
<220> FEATURE:
<223> OTHER INFORMATION: complement inhibitor

<400> SEQUENCE: 76

Ala Ala Glu Met Arg Trp Glu Phe Pro Leu
1               5                   10

<210> SEQ ID NO 77
<211> LENGTH: 10
<212> TYPE: PRT
<213> ORGANISM: Artificial Sequence
<220> FEATURE:
<223> OTHER INFORMATION: complement inhibitor

<400> SEQUENCE: 77
```

```
Ala Ala Glu Phe Arg Trp Glu Phe Pro Leu
1               5                   10

<210> SEQ ID NO 78
<211> LENGTH: 10
<212> TYPE: PRT
<213> ORGANISM: Artificial Sequence
<220> FEATURE:
<223> OTHER INFORMATION: complement inhibitor

<400> SEQUENCE: 78

Ala Ala Glu Pro Arg Trp Glu Phe Pro Leu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: complement inhibitor

<400> SEQUENCE: 79

Ala Ala Glu Ser Arg Trp Glu Phe Pro Leu
1               5                   10

<210> SEQ ID NO 80
<211> LENGTH: 10
<212> TYPE: PRT
<213> ORGANISM: Artificial Sequence
<220> FEATURE:
<223> OTHER INFORMATION: complement inhibitor

<400> SEQUENCE: 80

Ala Ala Glu Thr Arg Trp Glu Phe Pro Leu
1               5                   10

<210> SEQ ID NO 81
<211> LENGTH: 10
<212> TYPE: PRT
<213> ORGANISM: Artificial Sequence
<220> FEATURE:
<223> OTHER INFORMATION: complement inhibitor

<400> SEQUENCE: 81

Ala Ala Glu Trp Arg Trp Glu Phe Pro Leu
1               5                   10

<210> SEQ ID NO 82
<211> LENGTH: 10
<212> TYPE: PRT
<213> ORGANISM: Artificial Sequence
<220> FEATURE:
<223> OTHER INFORMATION: complement inhibitor

<400> SEQUENCE: 82

Ala Ala Glu Tyr Arg Trp Glu Phe Pro Leu
1               5                   10

<210> SEQ ID NO 83
<211> LENGTH: 10
<212> TYPE: PRT
<213> ORGANISM: Artificial Sequence
<220> FEATURE:
<223> OTHER INFORMATION: complement inhibitor

<400> SEQUENCE: 83

Ala Ala Glu Val Arg Trp Glu Phe Pro Leu
```

```
<210> SEQ ID NO 84
<211> LENGTH: 10
<212> TYPE: PRT
<213> ORGANISM: Artificial Sequence
<220> FEATURE:
<223> OTHER INFORMATION: complement inhibitor

<400> SEQUENCE: 84

Thr Ala Glu Val Arg Trp Glu Phe Pro Leu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: complement inhibitor

<400> SEQUENCE: 85

Thr Ala Ala Val Arg Trp Glu Phe Pro Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: complement inhibitor

<400> SEQUENCE: 86

Thr Ala Arg Val Arg Trp Glu Phe Pro Leu
1               5                   10

<210> SEQ ID NO 87
<211> LENGTH: 10
<212> TYPE: PRT
<213> ORGANISM: Artificial Sequence
<220> FEATURE:
<223> OTHER INFORMATION: complement inhibitor

<400> SEQUENCE: 87

Thr Ala Gln Val Arg Trp Glu Phe Pro Leu
1               5                   10

<210> SEQ ID NO 88
<211> LENGTH: 10
<212> TYPE: PRT
<213> ORGANISM: Artificial Sequence
<220> FEATURE:
<223> OTHER INFORMATION: complement inhibitor

<400> SEQUENCE: 88

Thr Ala Gly Val Arg Trp Glu Phe Pro Leu
1               5                   10

<210> SEQ ID NO 89
<211> LENGTH: 10
<212> TYPE: PRT
<213> ORGANISM: Artificial Sequence
<220> FEATURE:
<223> OTHER INFORMATION: comlpement inhibitor

<400> SEQUENCE: 89

Thr Ala His Val Arg Trp Glu Phe Pro Leu
1               5                   10
```

<210> SEQ ID NO 90
<211> LENGTH: 10
<212> TYPE: PRT
<213> ORGANISM: Artificial Sequence
<220> FEATURE:
<223> OTHER INFORMATION: complement inhibitor

<400> SEQUENCE: 90

Thr Ala Ile Val Arg Trp Glu Phe Pro Leu
1               5                   10

<210> SEQ ID NO 91
<211> LENGTH: 10
<212> TYPE: PRT
<213> ORGANISM: Artificial Sequence
<220> FEATURE:
<223> OTHER INFORMATION: complement inhibitor

<400> SEQUENCE: 91

Thr Ala Leu Val Arg Trp Glu Phe Pro Leu
1               5                   10

<210> SEQ ID NO 92
<211> LENGTH: 10
<212> TYPE: PRT
<213> ORGANISM: Artificial Sequence
<220> FEATURE:
<223> OTHER INFORMATION: complement inhibitor

<400> SEQUENCE: 92

Thr Ala Lys Val Arg Trp Glu Phe Pro Leu
1               5                   10

<210> SEQ ID NO 93
<211> LENGTH: 10
<212> TYPE: PRT
<213> ORGANISM: Artificial Sequence
<220> FEATURE:
<223> OTHER INFORMATION: complement inhibitor

<400> SEQUENCE: 93

Thr Ala Met Val Arg Trp Glu Phe Pro Leu
1               5                   10

<210> SEQ ID NO 94
<211> LENGTH: 10
<212> TYPE: PRT
<213> ORGANISM: Artificial Sequence
<220> FEATURE:
<223> OTHER INFORMATION: complement inhibitor

<400> SEQUENCE: 94

Thr Ala Phe Val Arg Trp Glu Phe Pro Leu
1               5                   10

<210> SEQ ID NO 95
<211> LENGTH: 10
<212> TYPE: PRT
<213> ORGANISM: Artificial Sequence
<220> FEATURE:
<223> OTHER INFORMATION: complement inhibitor

<400> SEQUENCE: 95

Thr Ala Pro Val Arg Trp Glu Glu Pro Leu
1               5                   10

<210> SEQ ID NO 96
<211> LENGTH: 10
<212> TYPE: PRT
<213> ORGANISM: Artificial Sequence
<220> FEATURE:
<223> OTHER INFORMATION: complement inhibitor

<400> SEQUENCE: 96

Thr Ala Ser Val Arg Trp Glu Glu Pro Leu
1               5                   10

<210> SEQ ID NO 97
<211> LENGTH: 10
<212> TYPE: PRT
<213> ORGANISM: Artificial Sequence
<220> FEATURE:
<223> OTHER INFORMATION: complement inhibitor

<400> SEQUENCE: 97

Thr Ala Thr Val Arg Trp Glu Glu Pro Leu
1               5                   10

<210> SEQ ID NO 98
<211> LENGTH: 10
<212> TYPE: PRT
<213> ORGANISM: Artificial Sequence
<220> FEATURE:
<223> OTHER INFORMATION: complement inhibitor

<400> SEQUENCE: 98

Thr Ala Trp Val Arg Trp Glu Glu Pro Leu
1               5                   10

<210> SEQ ID NO 99
<211> LENGTH: 10
<212> TYPE: PRT
<213> ORGANISM: Artificial Sequence
<220> FEATURE:
<223> OTHER INFORMATION: complement inhibitor

<400> SEQUENCE: 99

Thr Ala Tyr Val Arg Trp Glu Glu Pro Leu
1               5                   10

<210> SEQ ID NO 100
<211> LENGTH: 10
<212> TYPE: PRT
<213> ORGANISM: Artificial Sequence
<220> FEATURE:
<223> OTHER INFORMATION: complement inhibitor

<400> SEQUENCE: 100

Thr Ala Val Val Arg Trp Glu Glu Pro Leu
1               5                   10

<210> SEQ ID NO 101
<211> LENGTH: 10
<212> TYPE: PRT
<213> ORGANISM: Artificial Sequence
<220> FEATURE:
<223> OTHER INFORMATION: complement inhibitor

<400> SEQUENCE: 101

Thr Ala Glu Val Arg Trp Glu Phe Glu Leu
1               5                   10

<210> SEQ ID NO 102
<211> LENGTH: 10
<212> TYPE: PRT
<213> ORGANISM: Artificial Sequence
<220> FEATURE:
<223> OTHER INFORMATION: complement inhibitor

<400> SEQUENCE: 102

Thr Ala Glu Val Arg Trp Glu Phe Gln Leu
1               5                   10

<210> SEQ ID NO 103
<211> LENGTH: 10
<212> TYPE: PRT
<213> ORGANISM: Artificial Sequence
<220> FEATURE:
<223> OTHER INFORMATION: complement inhibitor

<400> SEQUENCE: 103

Thr Ala Glu Val Arg Trp Glu Phe Lys Leu
1               5                   10

<210> SEQ ID NO 104
<211> LENGTH: 10
<212> TYPE: PRT
<213> ORGANISM: Artificial Sequence
<220> FEATURE:
<223> OTHER INFORMATION: complement inhibitor

<400> SEQUENCE: 104

Thr Ala Glu Val Arg Trp Glu Phe Leu Leu
1               5                   10

<210> SEQ ID NO 105
<211> LENGTH: 10
<212> TYPE: PRT
<213> ORGANISM: Artificial Sequence
<220> FEATURE:
<223> OTHER INFORMATION: complement inhibitor

<400> SEQUENCE: 105

Thr Ala Glu Val Arg Trp Glu Phe Phe Leu
1               5                   10

<210> SEQ ID NO 106
<211> LENGTH: 10
<212> TYPE: PRT
<213> ORGANISM: Artificial Sequence
<220> FEATURE:
<223> OTHER INFORMATION: complement inhibitor

<400> SEQUENCE: 106

Thr Ala Glu Val Arg Trp Glu Phe Thr Leu
1               5                   10

<210> SEQ ID NO 107
<211> LENGTH: 10
<212> TYPE: PRT
<213> ORGANISM: Artificial Sequence
<220> FEATURE:
<223> OTHER INFORMATION: complement inhibitor

<400> SEQUENCE: 107

Thr Ala Glu Val Arg Trp Glu Phe Pro Glu
1               5                   10

<210> SEQ ID NO 108

```
<211> LENGTH: 10
<212> TYPE: PRT
<213> ORGANISM: Artificial Sequence
<220> FEATURE:
<223> OTHER INFORMATION: complement inhibitor

<400> SEQUENCE: 108

Thr Ala Glu Val Arg Trp Glu Phe Pro Lys
1               5                   10

<210> SEQ ID NO 109
<211> LENGTH: 10
<212> TYPE: PRT
<213> ORGANISM: Artificial Sequence
<220> FEATURE:
<223> OTHER INFORMATION: complement inhibitor

<400> SEQUENCE: 109

Thr Ala Glu Val Arg Trp Glu Phe Pro Gln
1               5                   10

<210> SEQ ID NO 110
<211> LENGTH: 10
<212> TYPE: PRT
<213> ORGANISM: Artificial Sequence
<220> FEATURE:
<223> OTHER INFORMATION: complement inhibitor

<400> SEQUENCE: 110

Thr Ala Glu Val Arg Trp Glu Phe Pro Thr
1               5                   10

<210> SEQ ID NO 111
<211> LENGTH: 10
<212> TYPE: PRT
<213> ORGANISM: Artificial Sequence
<220> FEATURE:
<223> OTHER INFORMATION: complement inhibitor

<400> SEQUENCE: 111

Thr Ala Glu Val Arg Trp Glu Phe Pro Trp
1               5                   10

<210> SEQ ID NO 112
<211> LENGTH: 10
<212> TYPE: PRT
<213> ORGANISM: Artificial Sequence
<220> FEATURE:
<223> OTHER INFORMATION: complement inhibitor

<400> SEQUENCE: 112

Glu Ala Glu Val Arg Trp Glu Phe Pro Leu
1               5                   10

<210> SEQ ID NO 113
<211> LENGTH: 10
<212> TYPE: PRT
<213> ORGANISM: Artificial Sequence
<220> FEATURE:
<223> OTHER INFORMATION: complement inhibitor

<400> SEQUENCE: 113

Lys Ala Glu Val Arg Trp Glu Phe Pro Leu
1               5                   10

<210> SEQ ID NO 114
<211> LENGTH: 10
```

<212> TYPE: PRT
<213> ORGANISM: Artificial Sequence
<220> FEATURE:
<223> OTHER INFORMATION: complement inhibitor

<400> SEQUENCE: 114

Gln Ala Glu Val Arg Trp Glu Phe Pro Leu
1               5                   10

<210> SEQ ID NO 115
<211> LENGTH: 10
<212> TYPE: PRT
<213> ORGANISM: Artificial Sequence
<220> FEATURE:
<223> OTHER INFORMATION: complement inhibitor

<400> SEQUENCE: 115

Leu Ala Glu Val Arg Trp Glu Phe Pro Leu
1               5                   10

<210> SEQ ID NO 116
<211> LENGTH: 10
<212> TYPE: PRT
<213> ORGANISM: Artificial Sequence
<220> FEATURE:
<223> OTHER INFORMATION: complement inhibitor

<400> SEQUENCE: 116

Trp Ala Glu Val Arg Trp Glu Phe Pro Leu
1               5                   10

<210> SEQ ID NO 117
<211> LENGTH: 10
<212> TYPE: PRT
<213> ORGANISM: Artificial Sequence
<220> FEATURE:
<223> OTHER INFORMATION: complement inhibitor

<400> SEQUENCE: 117

Thr Glu Glu Val Arg Trp Glu Phe Pro Leu
1               5                   10

<210> SEQ ID NO 118
<211> LENGTH: 10
<212> TYPE: PRT
<213> ORGANISM: Artificial Sequence
<220> FEATURE:
<223> OTHER INFORMATION: complement inhibitor

<400> SEQUENCE: 118

Thr Lys Glu Val Arg Trp Glu Phe Pro Leu
1               5                   10

<210> SEQ ID NO 119
<211> LENGTH: 10
<212> TYPE: PRT
<213> ORGANISM: Artificial Sequence
<220> FEATURE:
<223> OTHER INFORMATION: complement inhibitor

<400> SEQUENCE: 119

Thr Thr Glu Val Arg Trp Glu Phe Pro Leu
1               5                   10

<210> SEQ ID NO 120
<211> LENGTH: 10
<212> TYPE: PRT

```
<213> ORGANISM: Artificial Sequence
<220> FEATURE:
<223> OTHER INFORMATION: complement inhibitor

<400> SEQUENCE: 120

Thr Leu Glu Val Arg Trp Glu Phe Pro Leu
1               5                   10

<210> SEQ ID NO 121
<211> LENGTH: 10
<212> TYPE: PRT
<213> ORGANISM: Artificial Sequence
<220> FEATURE:
<223> OTHER INFORMATION: complement inhibitor

<400> SEQUENCE: 121

Thr Trp Glu Val Arg Trp Glu Phe Pro Leu
1               5                   10
```